United States Patent [19]

Chakravarty et al.

[11] Patent Number: 5,064,825
[45] Date of Patent: Nov. 12, 1991

[54] ANGIOTENSIN II ANTAGONISTS

[75] Inventors: Prasun K. Chakravarty, Edison; William J. Greenlee, Teaneck; Nathan B. Mantlo; Arthur A. Patchett, both of Westfield; William Schoen, Edison; Thomas F. Walsh, Westfield, all of N.J.

[73] Assignee: Merck & Co., Inc., Rahway, N.J.

[21] Appl. No.: 522,662

[22] Filed: May 16, 1990

Related U.S. Application Data

[63] Continuation-in-part of Ser. No. 360,673, Jun. 1, 1989, abandoned.

[51] Int. Cl.$^5$ .................. A61K 31/55; C07D 487/22
[52] U.S. Cl. ...................... 514/221; 514/81; 514/211; 540/490; 540/487; 540/502
[58] Field of Search .................. 540/502, 490, 487; 514/221, 211, 81

[56]  References Cited

U.S. PATENT DOCUMENTS

| | | | |
|---|---|---|---|
| 4,207,324 | 6/1980 | Matsumura et al. | 514/397 |
| 4,340,598 | 7/1982 | Furukawa et al. | 514/400 |
| 4,576,958 | 3/1986 | Wexler | 548/342 |
| 4,582,847 | 4/1986 | Furukawa et al. | 514/400 |

FOREIGN PATENT DOCUMENTS

| | | | |
|---|---|---|---|
| 0028834 | 5/1981 | European Pat. Off. | 548/252 |
| 0245637 | 11/1987 | European Pat. Off. | 548/252 |
| 0253310 | 1/1988 | European Pat. Off. | 548/252 |
| 0291969 | 5/1988 | European Pat. Off. | 548/252 |

OTHER PUBLICATIONS

P. G. Wong et al., *J. Pharmcol. Exp. Ther.*, "Nonpeptide Angiotension II Receptor Antagonists", 247(1), pp. 1–(1988).

P. K. Bridson et al., *Journal of Heterocyclic Chemistry*, "Cyclic Homologs of Xanthins", 25(4), pp. 1179–1182 (1988).

*Primary Examiner*—Richard L. Raymond
*Assistant Examiner*—Mark W. Russell
*Attorney, Agent, or Firm*—William H. Nicholson; Joseph F. DiPrima

[57]  ABSTRACT

Novel substituted imidazo-fused 7-member ring heterocycles of the formulae (I) and (Ia), which are useful as angiotensin II antagonists, are disclosed.

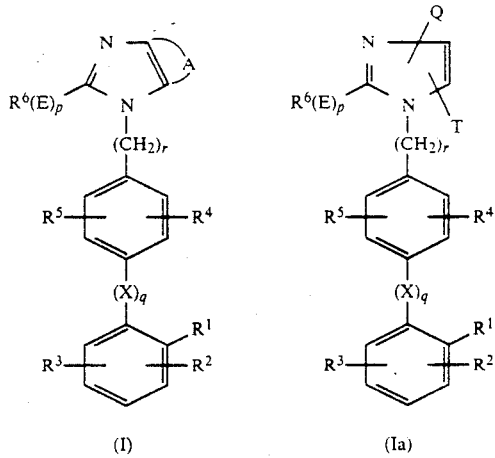

9 Claims, No Drawings

ANGIOTENSIN II ANTAGONISTS

BACKGROUND OF THE INVENTION

This application is a continuation-in-part of co-pending application Ser. No. 360,673 filed June 1, 1989 now abandoned.

Renin-angiotensin system (RAS) plays a central role in the regulation of normal blood pressure and seems to be critically involved in hypertension development and maintenance as well as congestive heart failure. Angiotensin II (A II), is an optapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; 291,969; 323,841; 324,377 and and in articles by A. T. Chiu, et al. [*Eur. J. Pharm. Exp. Therap*, 13–21 (1988)] and by P. C. Wong, et al. [*J. Pharm. Exp. Therap*, 247, 1–7(1988)]. All of the U.S. Pat. Nos., European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7 tetrahydro 2H-imidazo[4,5c]-pyridine-6-carboxylic acid and analogs thereof as antihypertensive specifically $Ca^{2+}$ channel blockers, and European Patent Application 323,841 discloses substituted pyrroles, pyrazoles and triazoles as angiotensin II antagonists.

BRIEF DESCRIPTION OF THE INVENTION

This invention is directed to novel substituted imidazo-fused 7-member ring heterocyclic compounds of the formula (I) and to novel substituted imidazo compounds of the formula (Ia) both of which are angiotension 11 antagonists and are useful in the treatment of hypertension and congestive heart failure. Specifically, the compounds of this invention contain an imidazole moiety which is substituted at the 1 and 2 positions and to which a seven member heterocyclic ring is fused at the 4 and 5 positions or which is substituted at the 4 and 5 positions. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed and claimed Further, methods of treating hypertension, congestive heart failure and elevated intraocular pressure are described and claimed.

DETAILED DESCRIPTION OF THE INVENTION

This invention relates to compounds of the formulae (I) and (Ia):

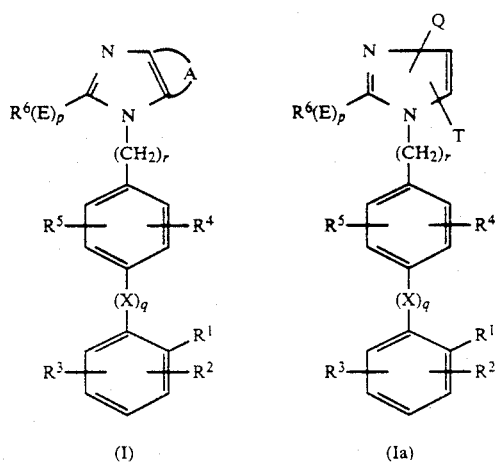

wherein:
$R^1$ is
(a) $-CO_2R^7$,
(b) $-SO_3R^8$,
(c) $-PO_3R^8R^8$,
(d) $-NHSO_2CF_3$,
(e) $-SO_2NHR^9$,
(f) $-CONHOR^9$,

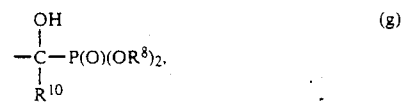

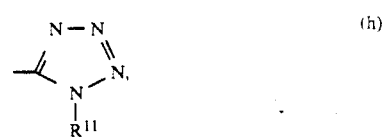

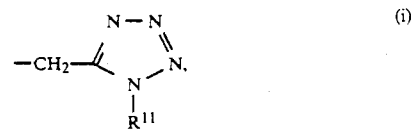

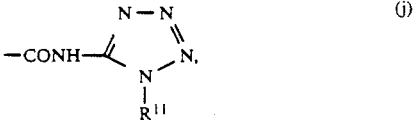

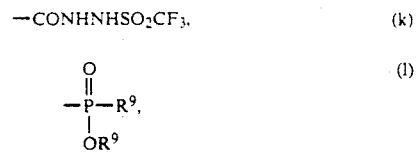

-continued

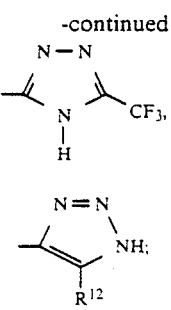

(o) —SONH—heteroaryl as defined below,
(p) —CH$_2$SO$_{NH}$—heteroaryl as defined below,
(q) —SO$_2$NH—CO—R$^{25}$,
(r) —CH$_2$SO$_2$NH—CO—R$^{25}$,
(s) —CONH—SO$_2$R$^{25}$,
(t) —CH$_2$COHN—SO$_2$R$^{25}$,
(u) —NHSO$_2$NHCO—R$^{25}$,
(v) —NHCONHSO$_2$R$^{25}$,
(w) —SO$_2$NHCONHR$^{25}$, or
(x) —CONHSO$_2$NHR$^{25}$
 wherein:
  heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —C$_1$–C$_4$—alkyl, —C$_1$–C$_4$—alkoxy, —CH$_3$, halo (Cl, Br, F, I), —NO$_2$, —CO$_2$H, —CO$_2$—C$_1$–C$_4$-alkyl, —NH$_2$, —NH(C$_1$–C$_4$-alkyl) and —N(C$_1$–C$_4$-alkyl)$_2$;

R$^2$ and R$^3$ are each independently
 (a) H,
 (b) halo Cl, Br, I, F),
 (c) NO$_2$,
 (d) NH$_2$,
 (e) C$_1$–C$_4$-alkylamino,
 (f) di(C$_1$–C$_4$-alkyl)amino
 (g) SO$_2$—NHR$^9$,
 (h) perfluoro-C$_1$–C$_4$-alkyl,
 (i) C$_1$–C$_4$-alkyl, or
 (j) C$_1$–C$_4$-alkoxy;

R$^4$ is
 (a) H, or
 (b) C$_1$–C$_4$-alkyl;

R$^{4a}$ is C$_1$–C$_6$-alkyl;

R$^5$ is
 (a) H,
 (b) halo,
 (c) NO$_2$,
 (d) C$_1$–C$_4$-alkyl,
 (e) C$_1$–C$_4$-acyloxy,
 (f) C$_3$–C$_7$-cycloalkyl
 (g) C$_1$–C$_4$-alkoxy,
 (h) —CO$_2$R$^7$,
 (i) —NHSO$_2$CH$_3$,
 (j) hydroxy C$_1$–C$_4$-alkyl,
 (k) C$_1$–C$_4$-alkylphenyl,
 (l) C$_1$–C$_4$-alkylnaphthyl,
 (m) C$_1$–C$_4$-alkylthio,
 (n) C$_1$–C$_4$-alkylsulfinyl,
 (o) C$_1$–C$_4$-alkylsulfonyl,
 (p) NH$_2$,
 (q) C$_1$–C$_4$-alkylamino,
 (r) di(C$_1$–C$_4$-alkyl)amino,
 (s) fluoro C$_1$–C$_4$-alkyl,
 (t) —CONHOR$^9$,
 (u) —SO$_2$—NHR$^9$,
 (v) phenyl,
 (w) naphthyl,
 (x) furyl,
 (y) perfluoro-C$_1$–C$_4$-alkyl,
 (z) C$_2$–C$_4$-alkenyl, or
 (aa) C$_2$–C$_4$-alkynyl;

R$^6$ is
 (a) C$_1$–C$_6$-alkyl,
 (b) C$_2$–C$_6$-alkenyl,
 (c) C$_2$–C$_6$-alkynyl,
 (d) substituted C$_1$–C$_6$-alkyl, substituted C$_2$–C$_6$-alkenyl or substituted C$_2$–C$_6$-alkynyl wherein the substituent is selected from the group consisting of
  (i) hydroxy,
  (ii) halo,
  (iii) amino,
  (iv) C$_1$–C$_4$-alkylamino,
  (v) di(C$_1$–C$_4$-alkyl)amino,
  (vi) carboxy,
  (vii) C$_1$–C$_4$-alkoxycarbonyl,
  (viii) C$_3$–C$_7$-cycloalkyl,
  (ix) phenyl, or
  (x) naphthyl,
 (e) phenyl,
 (f) naphthyl,
 (g) substituted phenyl or substituted naphthyl wherein the substituent is selected from the group consisting of
  (i) halo,
  (ii) C$_1$–C$_4$-alkyl,
  (iii) C$_1$–C$_4$-alkoxy,
  (iv) NO$_2$,
  (v) CF$_3$,
  (vi) SO$_2$—NR$^9$R$^{10}$,
  (vii) C$_1$–C$_4$-alkylthio,
  (viii) hydroxy,
  (ix) amino,
  (x) C$_3$–C$_7$-cycloalkyl,
  (xi) C$_3$–C$_{10}$-alkenyl, or
 (h) a heterocyclic moiety selected from the group consisting of:
  (i) 2-pyridyl,
  (ii) 4-pyridyl,
  (iii) 2-pyrimidyl,
  (iv) 6-pyrimidyl,
  (v) imidazoyl,
  (vi) thiazolyl,
  (vii) indolyl,
  (viii) thienyl,
  (ix) furyl,
  (x) benzothienyl,
  (xi) benzimidazoyl, or
 (i) C$_3$–C$_7$-cycloalkyl;

A is read in a clockwise direction and is selected from the group consisting of:

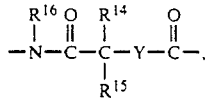 (a)

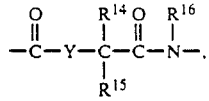 (b)

-continued

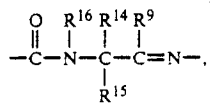 (c)

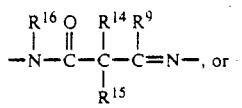 (d)

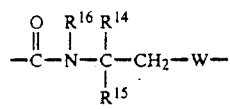 (e)

E is

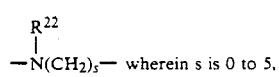 wherein s is 0 to 5, (a)

$-S(O)_x(CH_2)_s-$ wherein x is 0 to 2 and s is 0 to 5, (b)

 (c)

 (d)

$-O-$; (e)

p is 0 or 1;
X is

 (a)

$-O-$, (b)

$-S(O)_y-$ wherein y is 0 to 2, (c)

 (d)

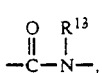 (e)

$-OCH_2-$, (f)

$-CH_2O-$, (g)

$-SCH_2-$, (h)

$-CH_2S-$, (i)

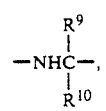 (j)

$NR^9SO_2$, (k)

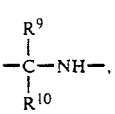 (l)

$-CH=CH-$, (m)

-continued $-CF=CF-$, (n)

$-CH=CF-$, (o)

$-CF=CH-$, (p)

$-CH_2CH_2-$, (q)

$-CF_2CF_2-$, (r)

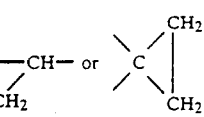 (s)

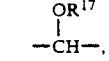 (t)

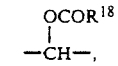 (u)

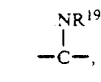 (v)

or

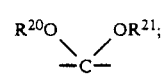 (w)

r is 1 or 2;
q is 0 or 1;
$R^7$ is
  (a) H,
  (b) $C_1-C_6$-alkyl,
  (c) phenyl, or
  (d) benzyl;
$R^8$ is
  (a) H, or

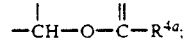 (b)

$R^9$ and $R^{10}$ are independently
  (a) H,
  (b) $C_1-C_6$-alkyl,
  (c) phenyl, or
  (d) benzyl;
$R^{11}$ is
  (a) H,
  (b) $C_1-C_6$-alkyl,
  (c) $C_2-C_4$-alkenyl, or
  (d) $C_1-C_4$-alkoxy-$C_1-C_4$-alkyl;
$R^{12}$ is
  (a) CN,
  (b) $NO_2$, or
  (c) $CO_2R^7$;
$R^{13}$ is
  (a) H,
  (b) $C_1-C_6$-alkyl,
  (c) $C_3-C_6$-cycloalkyl,
  (d) allyl or
  (e) benzyl;
Z is
  (a) $-O-$, $R^{13}$
|
—N—, or (c) —S(O)$_x$—;

$R^{14}$ and $R^{15}$ are independently
(a) H,
(b) $C_1$-$C_6$-alkyl,
(c) $C_2$-$C_6$-alkenyl,
(d) $C_2$-$C_6$-alkynyl,
(e) substituted $C_1$-$C_6$-alkyl, substituted $C_2$-$C_6$-alkenyl, or substituted $C_2$-$C_6$-alkynyl wherein the substituent is selected from the group consisting of
  (i) hydroxy,
  (ii) $C_1$-$C_4$-alkoxy,
  (iii) —N($R^4$)$_2$,
  (iv) —CON($R^4$)$_2$,
  (v) $CO_2R^7$,
  (vi) OC(O)$R^9$,
  (vii) guanidino, or
  (viii) $C_1$-$C_4$-alkylthio,
(f) phenyl,
(g) phenyl $C_1$-$C_4$-alkyl,
(h) substituted phenyl or substituted phenyl $C_1$-$C_4$ alkyl wherein the phenyl group is substituted with a member selected from the group consisting of
  (i) hydroxy,
  (ii) halo,
  (iii) $C_1$-$C_4$-alkyl,
  (iv) $C_1$-$C_4$-alkoxy,
(i) heterocyclic $C_1$-$C_4$-alkyl wherein the heterocyclic group is a member selected from the group consisting of
  (i) imidazolyl, or
  (ii) indolyl;

$R^{16}$ is
(a) H, or
(b) $C_1$-$C_6$-alkyl,
(c) $C_1$-$C_6$-alkyl substituted with hydroxy;

Y is
(a) —O—, or (b)
$R^{16}$
|
—N—;

W is
(a) —O—, (b)
$R^{22}$
|
—N—, or (c) —S—;

$R^{17}$ is
(a) H,
(b) $C_1$-$C_6$-alkyl;

$R^{18}$ is
(a) H,
(b) $C_1$-$C_6$-alkyl,
(c) $C_3$-$C_6$-cycloalkyl,
(d) aryl, or
(e) aryl-CH$_2$—; wherein aryl is phenyl or substituted phenyl wherein the substituents are members selected from the group consisting of halo (Cl, Br, F, I), Br, F, I), —NO$_2$, —CF$_3$, $C_1$-$C_4$-alkyl, $C_1$-$C_4$-alkoxy, —NH$_2$, —NH($C_1$-$C_4$-alkyl), —N($C_1$—$C_4$-alkyl)$_2$, —NHCO$_2$—$C_1$—$C_4$-alkyl, —OH —CO$_2$H, —CO$_2$—$C_1$—$C_4$-alkyl;

$R^{19}$ is
(a) —NR$^9$R$^{10}$,
(b) —OR$^{10}$,
(c) —NHCONH$_2$,
(d) —NHCSNH$_2$, (e)
—NHSO$_2$—⟨phenyl⟩—CH$_3$, or (f)
—NHSO$_2$—⟨phenyl⟩;

$R^{20}$ and $R^{21}$ are independently
(a) $C_1$-$C_4$-alkyl, or
(b) when taken together are —CH$_2$CH$_2$— or —CH$_2$CH$_2$CH$_2$—;

$R^{22}$ is
(a) H,
(b) $C_1$-$C_6$-alkyl,
(c) $C_3$-$C_6$-cycloalkyl,
(d) $C_1$-$C_4$-acyl,
(e) benzyl,
(f) phenyl, or
(g) allyl;

Q is
(a) —N($R^{24}$)CO—$R^{26}$,
(b) —NHCOR$^{26}$,
(c) —N($R^{24}$)SO$_2$R$^{26}$,
(d) —NHSO$_2$-$C_1$-$C_4$-alkyl,
(e) —N($R^4$)R$^{27}$;

T is
(a) —CO$_2$R$^{23}$,
(b) —CONHSO$_2$R$^{25}$,
(c) —CONR$^4$R$^{27}$,
(d) —CN,
(e) —tetrazol-5-yl;

$R^{23}$ is
(a) H,
(b) $C_1$-$C_6$-alkyl;

$R^{24}$ is
(a) $C_1$-$C_6$-alkyl,
(b) aryl or,
(c) aryl-CH$_2$—wherein aryl is as defined above;

$R^{25}$ is
(a) aryl as defined above,
(b) heteroaryl as defined above,
(c) $C_3$-$C_7$-cycloalkyl,
(d) $C_1$-$C_4$-alkyl optionally substituted with a substituents selected from the group consisting of aryl as defined above, heteroaryl as defined above, —OH, —SH, $C_1$-$C_4$-alkyl, —O($C_1$-$C_4$-alkyl), —S($C_1$-$C_4$-alkyl), —CF$_3$, halo (Cl, Br, F, I), —NO$_2$, —CO$_2$H, CO$_2$—$C_1$-$C_4$-alkyl, -NH$_2$, —NH($C_1$-$C_4$-alky), —$C_1$-$C_4$-alkyl)$_2$, —PO$_3$H, —PO(OH)(O—$C_1$-$C_4$-alkyl);
(e) perfluoro-$C_1$-$C_4$-alkyl;

$R^{26}$ is
(a) $C_1$-$C_4$-alkyl optionally substituted with aryl as defined above, —N($R^4$)$_2$, —NCO$_2$R$^{18}$, or —CO$_2$R$^4$,
(b) perfluoro-$C_1$-$C_4$-alkyl, (c) aryl as defined above,
(d) —N(R⁴)₂,
(e) $C_3$-$C_5$-cycloalkyl, or
(f)

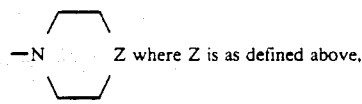

(g) heteroaryl as defined above;
$R^{27}$ is
(a) H,
(b) aryl as defined above, or
(c) $C_1$-$C_6$-alkyl optionally substituted with aryl as defined above, —OH, —$CO_2R^4$, or —N(R⁴)₂; and, the pharmaceutically acceptable salts thereof.

Except where specifically defined to the contrary, the terms "alkyl", "alkenyl", "alkynyl", "alkoxy" and "acyl" include both straight-chain and branch-chain species of the term.

One embodiment of the instant invention is represented by the formula (II)

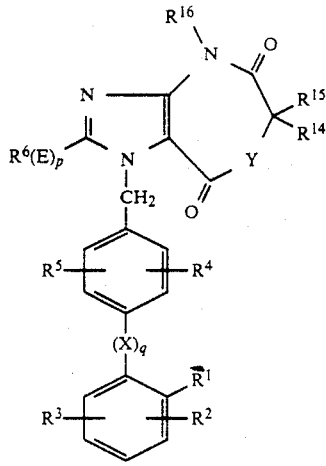

(II)

wherein:
$R^1$ is
(a) carboxy,
(b) $C_1$-$C_4$-alkoxycarbonyl,
(c) —NHSO₂CF₃, or

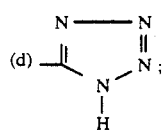

(d)

(e) —PO(OR⁹R⁹),
(f) —PO(OR⁹)₂,
(g) —SO₂NH-heteroaryl,
(h) —CH₂SO₂NH-heteroaryl,
(i) —SO₂NH—CO—R²⁵,
(j) —CH₂SO₂NH—CO—R²⁵,
(k) —CONH—SO₂R²⁵,
(l) —CH₂CONH—SO₂R²⁵,
(m) —NHSO₂NHCO—R²⁵,
(n) —NHCONHSO₂R²⁵,
(o) —SO₂NHCONHR²⁵,
$R^2$ and $R^3$ are independently (a) hydrogen,
(b) $C_1$-$C_4$-alkyl, or
(c) halo;
$R_4$ and $R_5$ are independently
(a) hydrogen,
(b) $C_1$-$C_6$-alkyl,
(c) $C_1$-$C_6$-alkoxy, or
(d) halo;
$R^6$ is
(a) $C_1C_6$-alkyl,
(b) $C_2$-$C_6$-alkenyl,
(c) $C_1$-$C_4$-alkoxy-$C_1$-$C_6$-alkyl,
(d) $C_1$-$C_4$-alkylthio-$C_1$-$C_6$-alkyl,
(e) $C_1$-$C_4$-alkoxy $C_2$-$C_6$ alkenyl, or
(f) $C_1$-$C_4$-alkylthio-$C_2$-$C_6$-alkenyl;
E is —S—;
p is 0 or 1;
X is (a) 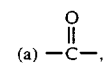

(b) —S— or
(c) —OCH₂—;
q is 0 or 1;
$R^{14}$ is H;
$R^{15}$ is
(a) H,
(b) $C_1$-$C_6$-alkyl,
(c) substituted $C_1$-$C_6$-alkyl wherein the substituent is selected from the group consisting of
    (i) hydroxy,
    (ii) amino,
    (iii) guanidino,
    (iv) $C_1$-$C_4$-alkylthio,
    (v) carboxy,
    (vi) carboxamido,
    (vii) $C_1$-$C_4$-alkoxycarbonyl, or
    (viii)

wherein $R^9$ is H, $C_1$-$C_6$-alkyl, or phenyl
(d) benzyl,
(e) 4-hydroxybenzyl,
(f) 3-indolylmethyl,
(g) 4 imidazolylmethyl, or
(h) Phenyl; and
$R^{16}$ is H or $C_1$-$C_4$-alkyl Y is
(a) —O—, (b) 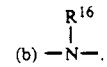

One class of this embodiment is the compounds of the formula (II) wherein $R^2$, $R^3$, $R^4$ and $R^5$ are hydrogen and p and q are 0. A sub-class of these compounds is the set of compounds wherein $R^1$ is carboxy, $C_1$-$C_4$-alkoxycarbonyl or tetrazole. Illustrating this sub-class are the compounds wherein $R^6$ is $C_1$-$C_6$-alkyl, $R^{15}$ and $R^{16}$ are hydrogen and Y is —NH—. Exemplifying this class are the following compounds.

(1) 2-butyl-1-(2'-carboxybiphen-4-yl)methyl-1,4,6,7-tetrahydroimidazo[4,5-e][1,4]-diazepine-5,8-dione; and, (2) 2-butyl-1-(2'-(tetrazol-5-yl)biphen-4-yl)-methyl-1,4,6,7-tetrahydroimidazo[4,5-e]-[1,4]diazepine-4-methyl-5,8-dione.

A second embodiment of the instant invention is represented by the formula (III)

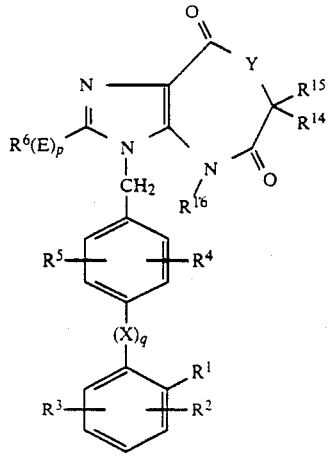

(III)

wherein:
R$^1$ is
  (a) carboxy,
  (b) C$_1$-C$_4$-alkoxy carbonyl,
  (c) —NHSO$_2$CF$_3$,

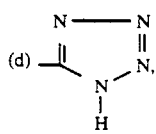

(e) —SO$_2$NH-heteroaryl,
  (f) —CH$_2$SO$_2$NH heteroaryl,
  (g) —SO$_2$NH—CO—R$^{25}$,
  (h) —CH$_2$SO$_2$NH—CO—R$^{25}$,
  (i) —CONH—SO$_2$R$^{25}$,
  (j) —CH$_2$CONH—SO$_2$R$^{25}$,
  (k) —NHSO$_2$NHCO—R$^{25}$,
  (l) —NHCONHSO$_2$R$^{25}$,
  (m) —SO$_2$NHCONHR$^{25}$, or
  (n) —CONHSO$_2$NHR$^{25}$ R$^2$ and R$^3$ are independently
  (a) hydrogen,
  (b) C$_1$-C$_4$ alkyl, or
  (c) halo;

R$^4$ and R$^5$ are independently
  (a) hydrogen,
  (b) C$_1$-C$_6$ alkyl,
  (c) C$_1$-C$_6$-alkoxy, or
  (d) halo;

R$^6$ is
  (a) C$_1$-C$_6$-alkyl,
  (b) C$_2$-C$_6$-alkenyl,
  (c) C$_1$-C$_4$-alkoxy-C$_1$-C$_6$-alkyl,
  (d) C$_1$-C$_4$-alkylthio-C$_1$-C$_6$-alkyl,
  (e) C$_1$-C$_4$-alkoxy-C$_2$-C$_6$-alkenyl, or
  (f) C$_1$-C$_4$-alkylthio C$_2$-C$_6$-alkenyl;

E is —S—;
p is 0 or 1;
X is (a) , (b) —S—or
(c) —OCH$_2$;

q is 0 or 1;
R$^{14}$ is H;
R$^{15}$ is
  (a) H,
  (b) C$_1$-C$_6$ alkyl,
  (c) substituted C$_1$-C$_6$-alkyl wherein the substituent is selected from the group consisting of:
    (i) hydroxy,
    (ii) amino,
    (iii) guanidino,
    (iv) C$_1$-C$_4$-alkylthio,
    (v) carboxy,
    (vi) carboxamido,
    (vii) C$_1$-C$_4$-alkoxycarbonyl, or

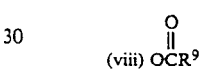
  (viii) OCR$^9$ wherein R$^9$ is H, C$_1$-C$_6$-alkyl, or phenyl (d) benzyl,
  (e) 4-hydroxybenzyl,
  (f) 3-indolylmethyl,
  (g) 4-imidazolylmethyl, or
  (h) phenyl; and R$^{16}$ is H or C$_1$-C$_4$-alkyl Y is
  (a) —O—, (b) .

One class of this embodiment is the compounds of the formula (III) wherein R$^2$, R$^3$, R$^4$ and R$^5$ are hydrogen and p and q are 0. A sub-class of these compounds is the set of compounds wherein R$^1$ is carboxy, C$_1$-C$_4$ alkoxycarbonyl or tetrazole. Illustrating this sub-class are the compounds wherein R$^6$ is C$_1$-C$_6$-alkyl, R$^{15}$ and R$^{16}$ are hydrogen and Y is —NH—. Exemplifying this class are the following compounds.

(1) 2-butyl 3-(2'carboxybiphen-4-yl)methyl-3,4,6,7-tetrahydroimidazo[4,5-e][1,4]-diazepine-5,8-dione; and,
(2) 2-butyl-3-(2'-(tetrazol-5-yl)biphen-4-yl)-methyl-3,4,6,7-tetrahydroimidazo[4,5-]-[1,4]diazepine-5,8-dione.

A third embodiment of the instant invention is represented by the formula (IV)

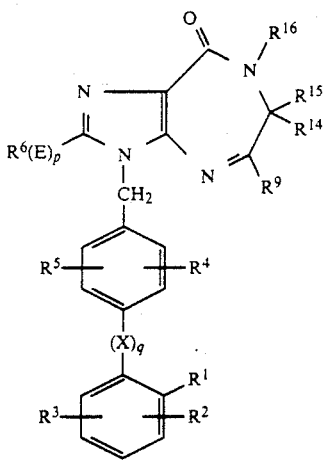

wherein:
R¹ is
 (a) carboxy,
 (b) $C_1$–$C_4$-alkoxy carbonyl,
 (c) —NHSO$_2$CF$_3$, or

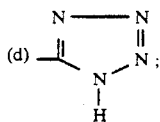

R² and R³ are independently
 (a) hydrogen,
 (b) $C_1$–$C_4$-alkyl, or
 (c) halo;
R⁴ and R⁵ are independently
 (a) hydrogen,
 (b) $C_1$–$C_6$ alkyl,
 (c) $C_1$–$C_6$-alkoxy, or
 (d) halo;
R⁶ is
 (a) $C_1$–$C_6$-alkyl,
 (b) $C_2$–$C_6$-alkenyl,
 (c) $C_1$–$C_4$-alkoxy-$C_1$–$C_6$-alkyl,
 (d) $C_1$–$C_4$-alkylthio-$C_1$–$C_6$-alkyl,
 (e) $C_1$–$C_4$-alkoxy-$C_2$–$C_6$-alkenyl, or
 (f) $C_1$–$C_4$-alkylthio-$C_2$–$C_6$-alkenyl;
R⁹ is
 (a) H,
 (b) $C_1$–$C_6$-alkyl, or
 (c) phenyl;
E is —S—;
p is 0 or 1;
X is

(b) —S— or
 (c) —OCH$_2$—;
q is 0 or 1;
R¹⁴ is H;
R¹⁵ is
 (a) H,
 (b) $C_1$–$C_6$-alkyl, (c) substituted -alkyl wherein the substituent is selected from the group consisting of
  (i) hydroxy,
  (ii) amino,
  (iii) guanidino,
  (iv) $C_1$–$C_4$-alkylthio,
  (v) carboxy,
  (vi) carboxamido,
  (vii) $C_1$–$C_4$-alkoxycarbonyl, or

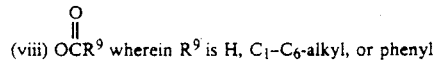

(d) benzyl,
 (e) 4-hydroxybenzyl,
 (f) 3-indolylmethyl,
 (g) 4-imidazolylmethyl, or
 (h) phenyl; and
R¹⁶ is H or $C_1$–$C_6$-alkyl One class of this embodiment is the compounds of the formula (IV) wherein R², R³, R⁴ and R⁵ are hydrogen and p and q are 0. A sub-class of these compounds is the set of compounds wherein R¹ is carboxy, $C_1$–$C_4$-alkoxycarbonyl or tetrazole. Illustrating this sub-class are the compounds wherein R⁶ is $C_1$–$C_6$-and R⁹, R¹⁵ and R¹⁶ are hydrogen. Exemplifying this class are the following compounds.
 (1) 2-butyl-3-(2'-carboxybiphen-4-yl)methyl-6,7-dihydroimidazo[4,5-e][1,4]diazepine-8-(3H)-one; and,
 (2) 2-butyl-3-(2'-(tetrazol-5-yl)biphen-4-yl)-methyl-6,7-dihydroimidazo[4,5-e][1,4]diazepine-8(3H)-one.

One embodiment of the formula (Ia) compounds of the invention are those wherein R², R³ R⁴ and R⁵ are hydrogen and p and q are o. A sub-class of these compounds are those wherein R⁶ is $C_1$–$C_6$-alkyl and r is 1. Exemplifying this class are the following compounds:
 (1) 4-Amino-2-butyl 5-carbomethoxy 1-[(2'-carboxybiphen-4-yl)methyl]-imidazole;
 (2) 2-Butyl-5-carbomethoxy-1 [(2'carboxybiphen-4yl)methyl]-4-methylamino-imidazole;
 (3) 2-Butyl-5-carbomethoxy-1-[(2'-carboxybiphen-4-yl)methyl]-4-dimethylaminoimidazole;
 (4) 4-Amino-2-butyl-5-carbomethoxy-1-[(Z'-(tetra-zol-5-yl)biphen-4-yl)methyl]-imidazole;
 (5) 4-Amino-5-carbomethoxy-Z propyl-1-[(Z'-(tetrazol-5-yl)biphen-4-yl)methyl]imidazole;
 (6) 5-Amino-4-carbomethoxy-2-propyl 1-[(2'-(tetrazol-5-yl)biphen-4-yl)methyl]-imidazole;
 (7) 2-Butyl-5-carbomethoxy-4-methylamino-1-[(2'-(tetrazol-5-yl)biphen-4-yl)methyl]imidazole;
 (8) 2-Butyl-4-carbomethoxy-5-methylamino-1-[(2'-(tetrazol-5-yl)biphen 4-yl)methyl]-imidazole;
 (9) 2-Butyl 5-carbomethoxy-4-dimethylamino-1-[(2'-(tetrazol-5-yl)biphen 4-yl)methyl]-imidazole:
 (10) 4-Benzylamino-Z-butyl-5-carbomethoxy-1-[(Z'-(tetrazol-5-yl)biphen 4-yl)methyl]-imidazole;
 (11) 4-(N-Benzyl N-methyl)amino 2-butyl-5-carbomethoxy-1-[(2'-(tetrazol-5-yl)biphen-4-yl)methyl]-imidazole;
 (12) 2-Butyl-5-carbomethoxy-4-(pyrrolidin-1-yl)-1-[(2'-(tetrazol-5-yl)biphen-4-yl)methyl]-imidazole;
 (13)-4-Acetamido-Z-butyl-5-carbomethoxy-1-[(2'-(tetrazol-5-yl)biphen-4-yl)methyl-]-imidazole:
 (14)-5-Acetamido-2-butyl-4-carbomethoxy-1-[-(2'-(tetrazol-5-yl)biphen-4-yl)methyl]imidazole;
 (15) 2-Butyl-5-carbomethoxy-4-(N-methyl)acetamido-1-[(2'-(tetrazol-5-yl)biphen-4-yl)methyl]imidazole;

(16) 2-Butyl-5-carbomethoxy-4-(N-phenyl)acetamido-1-[(2'-(tetrazol-5-yl)biphen 4-yl)methyl]imidazole;
(17) 2-Butyl-5-carboxy-4-(N-phenyl)acetamide 1(2'-(tetrazol-5-yl)biphen-4-yl)methyl]imidazole;
(18) 2-Butyl-5-carbomethoxy-4-(N-(2-chloro)phenyl)acetamido-1 [(2 -(tetrazol 5-yl)biphen 4 yl)-methyl]-imidazole;
(19) 2-Butyl-5-carbomethoxy-4-[N-(2-chloro)phenylmethyl]acetamido-1-[(2'-(tetrazol-5-yl)biphen-4-yl)methyl]-imidazole;
(20) 2-Butyl-5-carboxy-4-(N-methyl)acetamido-1-[(2'-(tetrazol-5-yl)biphen-4-yl)methyl]-imidazole;
(21) 2-Butyl-5-carboxy-4-(N-methyl)benzamido-1-[(2'-(tetrazol-5-yl)biphen-4-yl)methyl]-imidazole;
(22) 2 Butyl-5-carboxy-4-(N-ethyl)trifluoroacetamido-1-[(2'-(tetrazol-5-yl)biphen-4 yl)-methyl]-imidazole;
(23) 2-Butyl 5-carboxy-4-(N-methyl)butanamido-1-[(2'-(tetrazol-5-yl)biphen 4-yl)methyl]-imidazole;
(24) 4-Acetoxyacetamido-2-butyl-5-carbomethoxy-1-[(2'-(tetrazol-5-yl)biphen-4-yl)methyl]-imidazole;
(25) 4-(Aminoacetyl)amino-2-butyl-5-carbomethoxy-1 2'(tetrazol-5-yl)biphen-4-yl)methyl]imidazole;
(26) 2-Butyl-5-carbomethoxy-4-(N-phenyl)acetamido-1-[(2'-(N-phenylsulfonyl)carboxamidobiphen-4-yl)methyl]-imidazole;
(27) 4-Acetamido-2-butyl-5-carboxy 1-[(2'-(phenyl-sulfonyl)carboxamidobiphen-4-yl)methyl]imidazole;
(28) 4-Acetamido-2-butyl-5-carboxy-1-[(2'-(N-benzoyl)sulfonamidobiphen-4-yl)methyl]imidazole;
(29) 4-Acetamido-2-butyl-5-carboxy-1-[(2'-(N-acetyl)sulfonamidobiphen-4-yl)methyl]-imidazole;
(30) 2-Butyl-4-methylamino-5-carboethoxy-1-(2'-carboxybiphen-4-yl)methylimidazole; and,
(31) 2-Butyl-4-dimethylamino-5-carboethoxy-1-(2'-carboxybiphen-4-yl)methylimidazole.

| LIST OF ABBREVIATIONS USED | |
|---|---|
| Reagents: | |
| NS | N-bromosuccinimide |
| AIBN | Azo(bi)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| Im | imidazole |
| AcSK | potassium thioacetate |
| P-TsOH | p-toluenesulfonic acid |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| OTs | OSO$_2$-(4-methyl)phenyl |
| OMs | OSO$_2$CH$_3$ |
| Ph | phenyl |
| FAB-MS (FABMS) | Fast atom bombardment mass spectroscopy |
| NOE | Nuclear Overhauser Effect |
| SiO$_2$ | silica gel |
| trityl | triphenylmethyl |

The compounds (I) of the present invention can be prepared from intermediates such as those of formula (1):

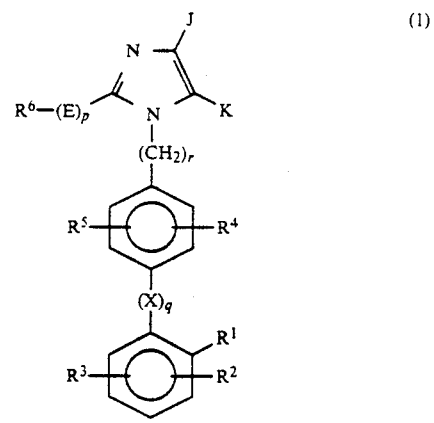

wherein J and K are respectively:
(a) CONR$^{16}$, NHR$^{16}$;
(b) NHR$^{16}$, CONHR$^{16}$;
(c) CO$_2$R$^7$, NHR$^{16}$;
(d) NHR$^{16}$, CO$_2$R$^7$;
(e) CO$_2$R$^7$, halo;
(f) halo, CO$_2$R$^7$;
(g) SH, CO$_2$R$^7$;
(h) CO$_2$R$_7$, SH;

Intermediates (1) are converted to products (I) by cyclization of J to K by treatment with a bidentate agent in an alkylation or condensation procedure as described in detail below. This cyclization introduces the fused 7-membered ring heterocycle of formula (I).

Intermediates (1) can be prepared as shown in Scheme 1 by treatment of an alkylating agent (2) wherein L is a good leaving group such as C$_1$, Br, I, O-mesyl or 0-tosyl and an imidazole (7) wherein J and K are independently halo, CONHR$^{16}$, CO$_2$R$^7$, NHR$^{16}$ moieties (R7=H). The alkylation reaction of Scheme 1 is conveniently carried out in anhydrous dimethyl formamide in the presence of bases such as sodium hydride or potassium t-butoxide for a period of 1-24 hours at temperatures of 20°-100° C. Substituent groups on alkylating agent (2) and imidazole (7) may need to be suitably protected. Examples of such protecting groups can be found in the text by T. W. Greene, Protective Groups In Organic Synthesis, John Wiley & Sons, 1981. Chromatography on silica gel is employed to separate isomers and to remove side products which may arise from alkylation on NHR$^{16}$ when this substituent is present.

Scheme 1

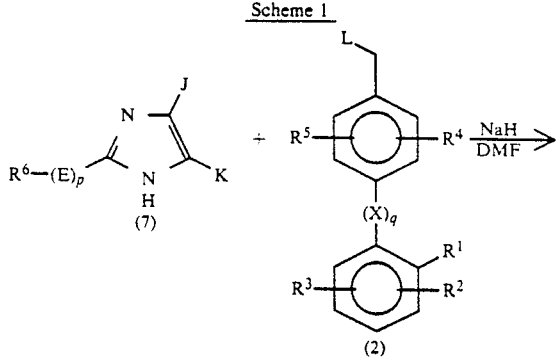

-continued
Scheme 1

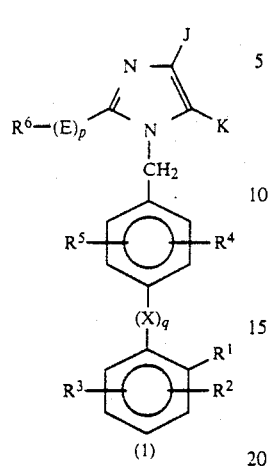
(1)

Alkylating agent (2) may be prepared as described in EPO publications 253,210 and 291,969 and the references cited therein. A useful method to prepare the preferred alkylating agents 6a, 6b and 6c is shown in reaction Scheme 2.

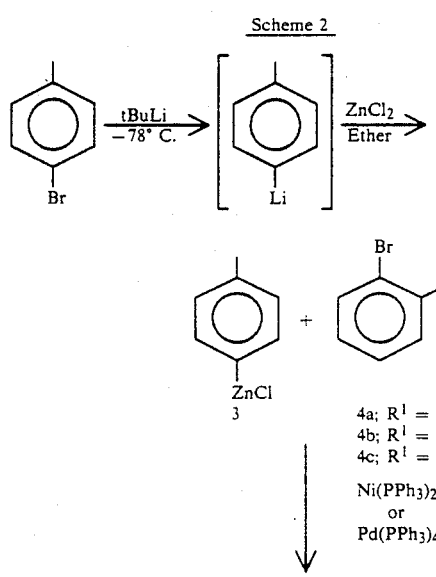

-continued
Scheme 2

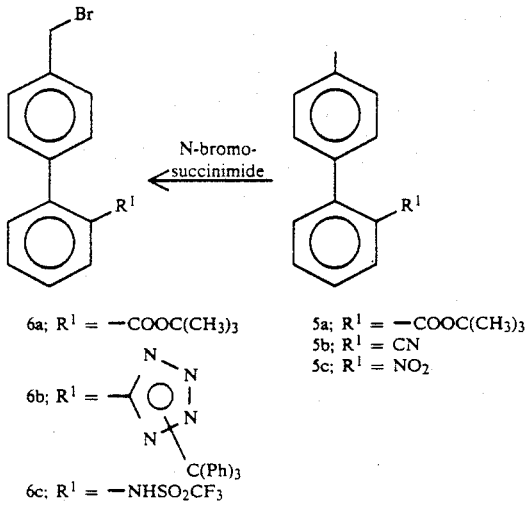

As outlined in Scheme 2, 4-bromotoluene is treated with t-BuLi followed by the addition of a ZnCl$_2$ solution to yield an organozinc compound (3). Compound (3) is then coupled with 4a or 4b in the presence of a Ni(PPh$_3$)$_2$Cl$_2$ catalyst to produce the desired biphenyl compound 5a or 5b. Similarly, 1-iodo-2-nitrobenzene (4c) is coupled with organozinc compound (3) in the presence of a Pd(PPh$_3$)$_4$ catalyst (prepared by treating Cl$_2$Pd(PPh$_3$)$_2$ with (i-Bu)$_2$AlH (2 equiv.)) to yield the biphenyl compound (5c). Precursors 5a, 5b and 5c are converted to halomethyl derivatives 6a, 6b and 6c respectively according to procedures described in EPO publications 253,310 and 291,969.

The imidazoles (7) required in alkylation Scheme 1 can be prepared by a number of methods well known in the literature including those described in EPO publication 253,310. A useful method of generating compound (7) wherein J and K are NH$_2$ and CONHR$^{16}$ or CO$_2$R$^7$ and p is zero is illustrated in Scheme 3.

Scheme 3

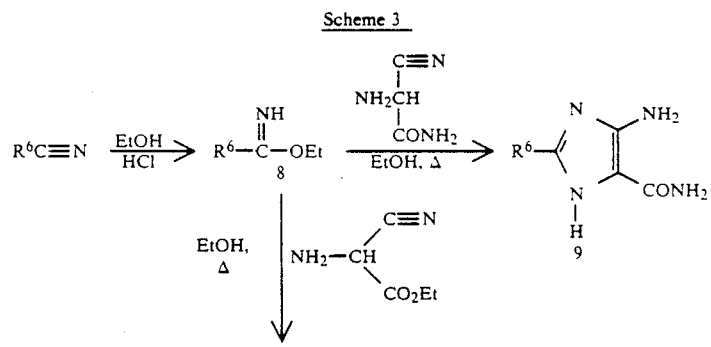

Scheme 3
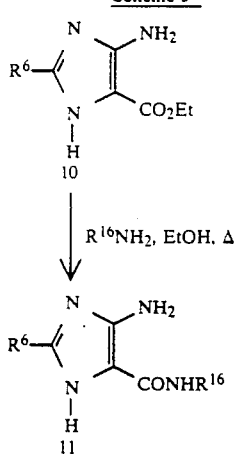
The synthesis of intermediate (1) wherein J is $NHR^{16}$ and K is $CONHR^{16}$ or $CO_2R^7$ ($R^7$=Ethyl) and p is zero can be accomplished by the alkylation of the cyanoamidine (13) with benzylic halide or pseudohalide (2) as outlined in Scheme 4.
Scheme 4
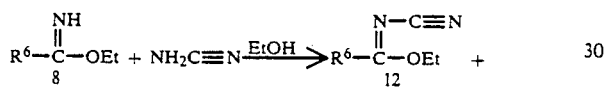
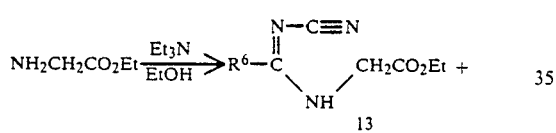
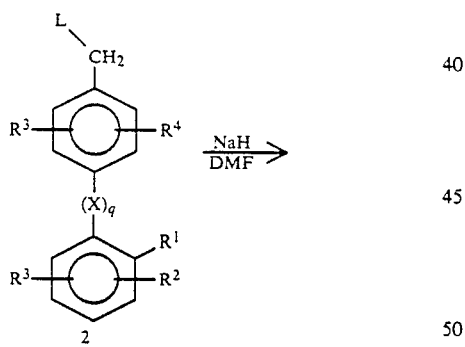
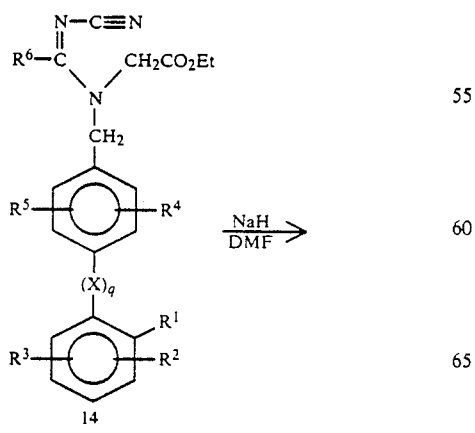
-continued
Scheme 4
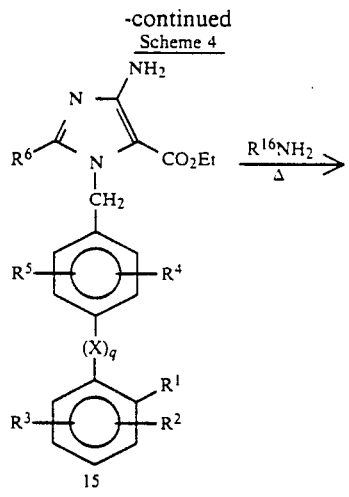
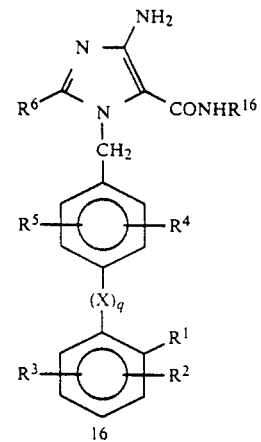

-continued
Scheme 4

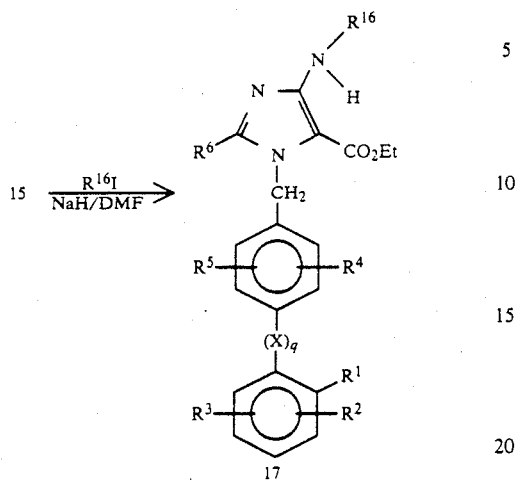

-continued
Scheme 5

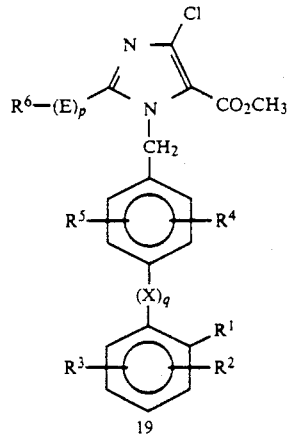

Cyanoamidine (13) is prepared according to the methods described by Edenhofer, *Helv. Chim Acta*, 58, 2192(1975).

Cyanoamidine (13) is alkylated employing the appropriately protected alkylating agent (2). For example, an $R^1$ carboxyl group can be conveniently protected as a t-butyl ester and an $R^1$ tetrazole group n N-trityl derivative The alkylated cyanomidine (14) is purified by silica gel chromatography as is the ring-closed product (15). Conversion of (15) to amide (16) can be accomplished by heating the ester with $R^{16}NH_2$ in an inert solvent such as ethanol. Compound (15) can be alkylated on the amino moiety using a small excess of $R^{16}$-I in DMF in the presence of NaH.

Compounds of formula (1) wherein J and K are either Cl and $CH_2OH$ or $CH_2OH$ and Cl respectively are also useful intermediates the preparations of which are described in EPO publication 253,310. The primary alcohol moiety in these compounds, $CH_2OH$, can be oxidized directly to the corresponding —$CO_2CH_3$ ester groups using $MnO_2$ in the presence of NaCN and acetic acid in methanol as illustrated in Scheme 5.

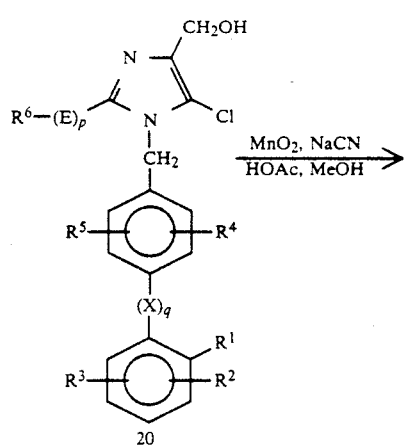

Scheme 5

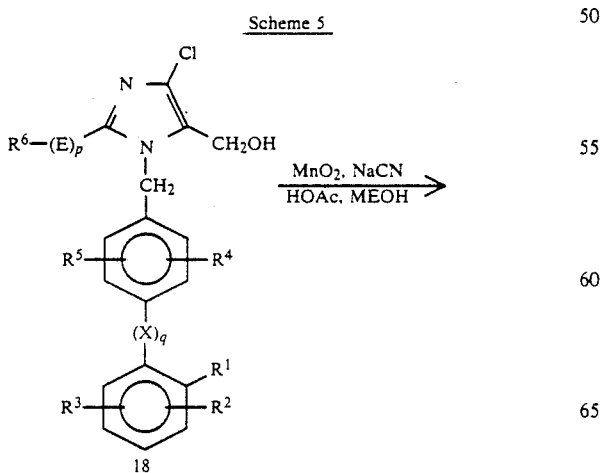

Compounds (19) and (21) from Scheme 5 can be further converted to thiol compounds as illustrated by the methodology of Scheme 6. Scheme 6 also illustrates an alternate route to amino compounds (22) which involves azide displacement of Cl followed by hydrogenation.

Scheme 6

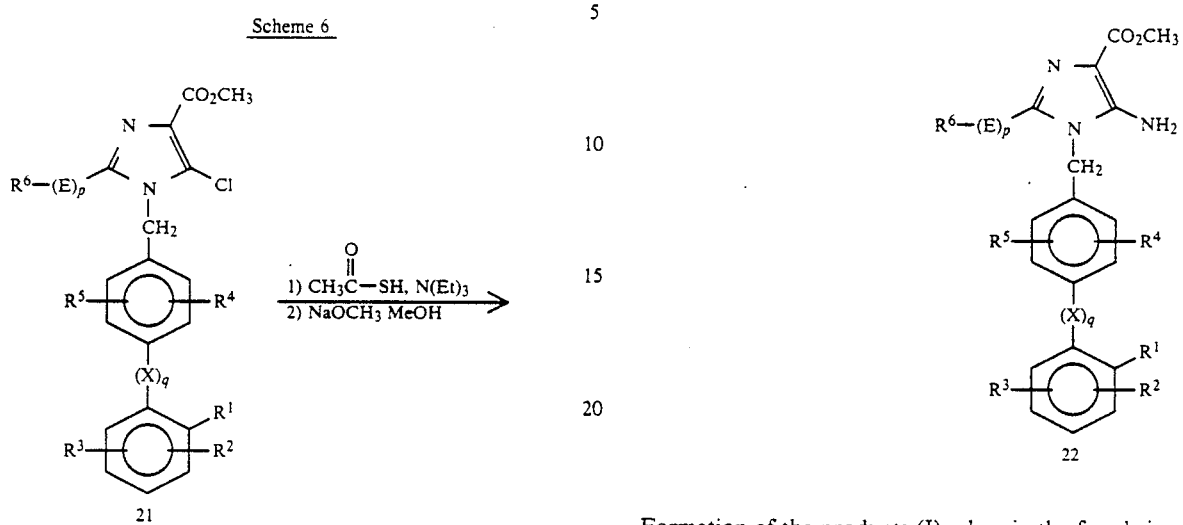

Scheme 6 —continued

Formation of the products (I) wherein the fused ring A contains $Y=NR^{16}$ is carried out from intermediates (1) wherein J and K are (NHR$^{16}$, CONHR$^{16}$) or (CONHR$^{16}$, NHR16) respectively by treating (1) in DMF with $L-C(O)-C(R^{14})(R^{15})$-L in the presence of a tertiary amine such as triethylamine. L is a leaving group which preferably is a halo group. When J or K is CO$_2$R$^7$ and R7=H then Y in the resultant products is oxygen. The transformations illustrated in scheme 7 with intermediate (16) are analogous to transformations which can be employed to synthesize similarly substituted benzodiazepines.

Scheme 7

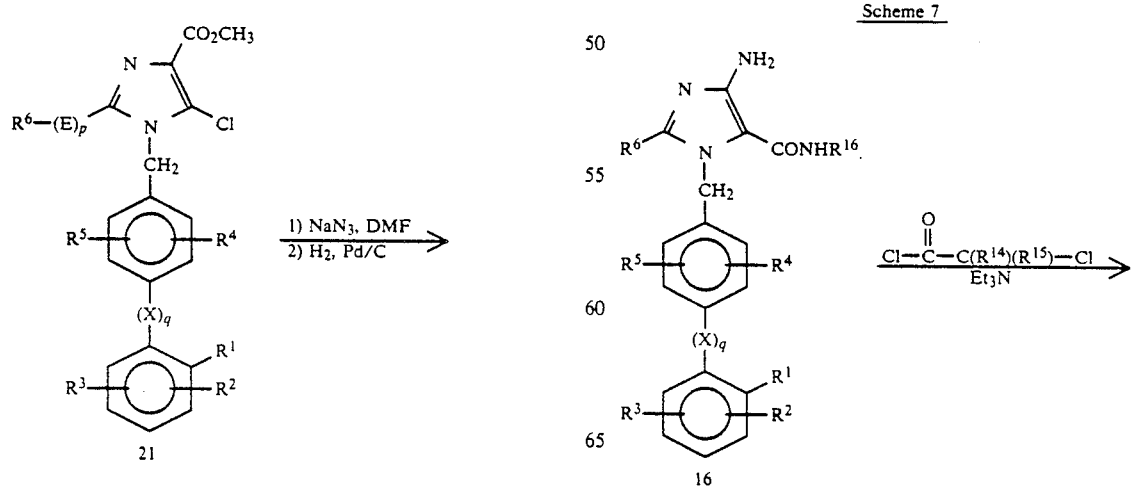

-continued
Scheme 7

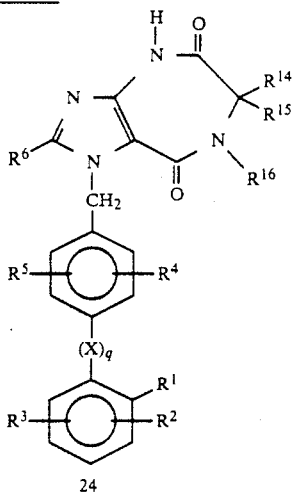

24

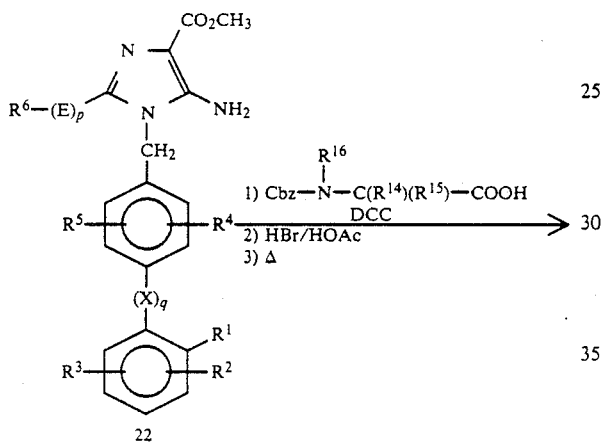

22

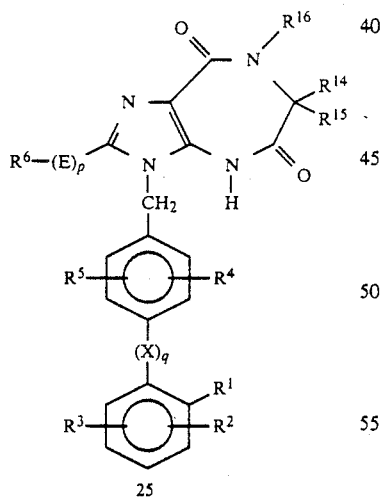

25

Scheme 7 also provides an alternate route to generate products (I) wherein Y is NR$^{16}$. In this sequence N-protected amino acids are used to acylate intermediate 1) wherein J or K is NR$_{16}$, by employing either an acyl halide, or a standard carboxyl activating reagent such as dicyclohexylcarbodiimide (DCC) or (benzotriazol-1-yl)oxytris(dimethylamino) phosphonium hexafluorophosphate (BOP). The N-protecting group of the amino acid such as the carbobenzyloxy (Cbz), t-butoxycarbonyl (t-BOC) or the fluorenylethylmethoxyloxycarbonyl (FMOC) group is removed according to standard peptide synthetic conditions. The final ring forming step is made by heating this intermediate in an alcoholic solvent or by saponifying the imidazole CO$_2$R$^7$ group to yield a carboxylic acid which is reacted with NR$^{16}$ using carboxyl activating reagents such as DCC or polyphosphoric acid.

Following the methodology of the above described transformation of Scheme 7, if J and K are SH and CO$_2$R$^7$, as illustrated by intermediate (23), and the ring forming reagent is HNR$^{16}$C(R$^{14}$)(R$^{15}$)CH$_2$Cl, it is possible to form products of formula (I) wherein A is —CON(R$^{16}$)—C(R$^{14}$)(R$^{15}$)—CH$_2$—W— or —W—CH—C(R$^{14}$) (R$^{15}$)—N(R$^{16}$)CO—and W is S.

The preparation of products (I) wherein A is —CON(R$^{16}$)—C(R$^{14}$)(R$^{15}$)—C(R$^9$)=N— is carried out in Scheme 8. The final ring closure which involves a dehydration to yield an amine can be assisted by heating in the presence of molecular sieves and acetic acid in an inert solvent such as dioxane or employing polyphosphoric acid as the dehydrating agent.

Scheme 8

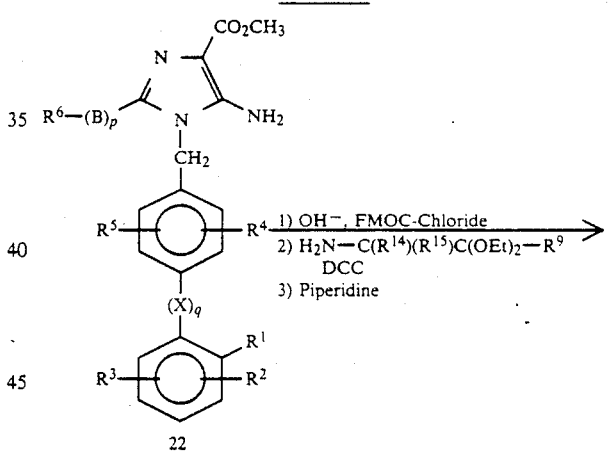

22

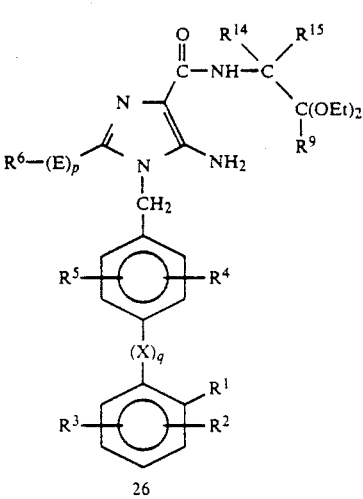

26

-continued
Scheme 8

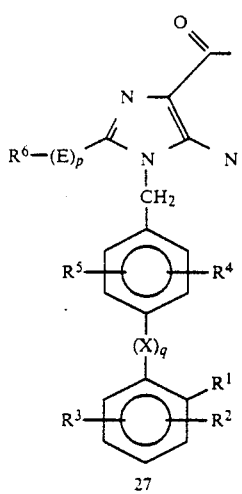

-continued
Scheme 9

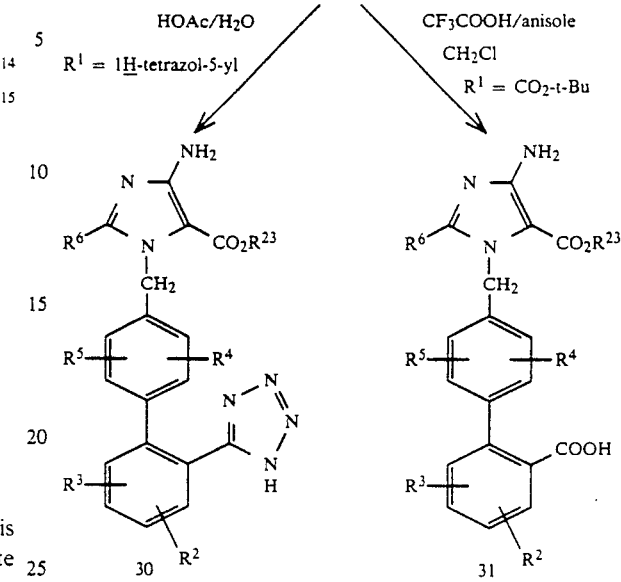

Compounds of formula (Ia) where Q is NH$_2$ and T is CO$_2$R$^{23}$ are prepared as shown in Scheme 9. Imidate (12) (prepared as described in Scheme 4) is converted to amidine 28 which is sequentially alkylated and cyclized by treatment with sodium hydride and agent (2) to give intermediate (29). Scheme 9 also illustrates the deprotection of intermediate (29) where R$^1$ is either tetrazole or CO$_2$tBu.

Acylation of intermediate (29) can be accomplished by treatment with an acid chloride as shown in Scheme 10. Amide (30) is then obtained after appropriate deprotection of R$^1$ as described in Scheme 9.

Scheme 9

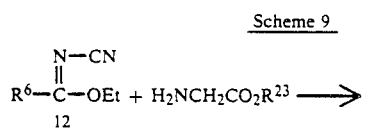

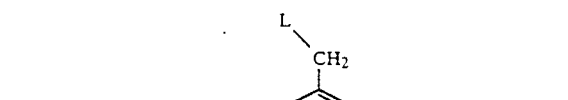

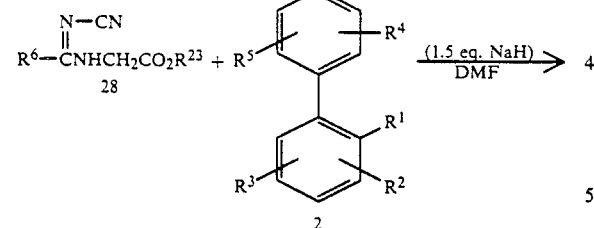

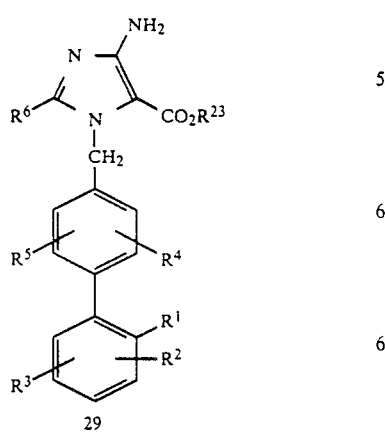

Scheme 10

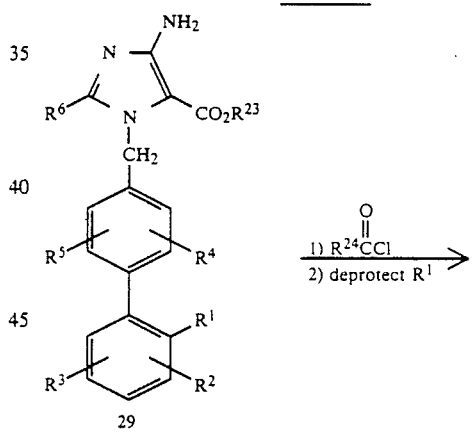

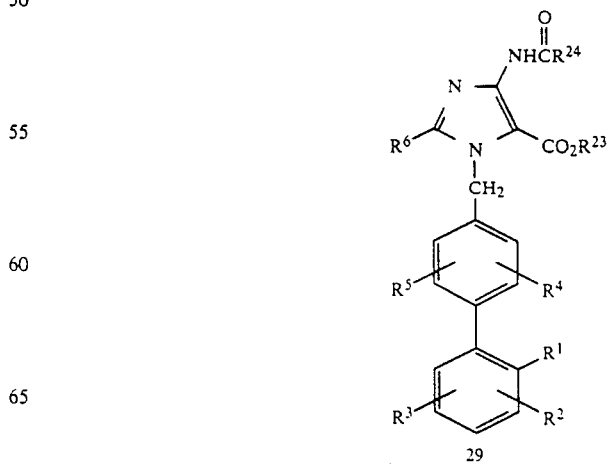

Alkylation of intermediate (29) is accomplished by treatment with a strong base such as sodium hydride and an alkylating agent as indicated by Scheme 11. A second alkyl group can be introduced by the same method with intermediate (31) as substrate. Deprotection of $R^1$ affords the mono-and di-alkylated compounds (33) and (34), respectively.

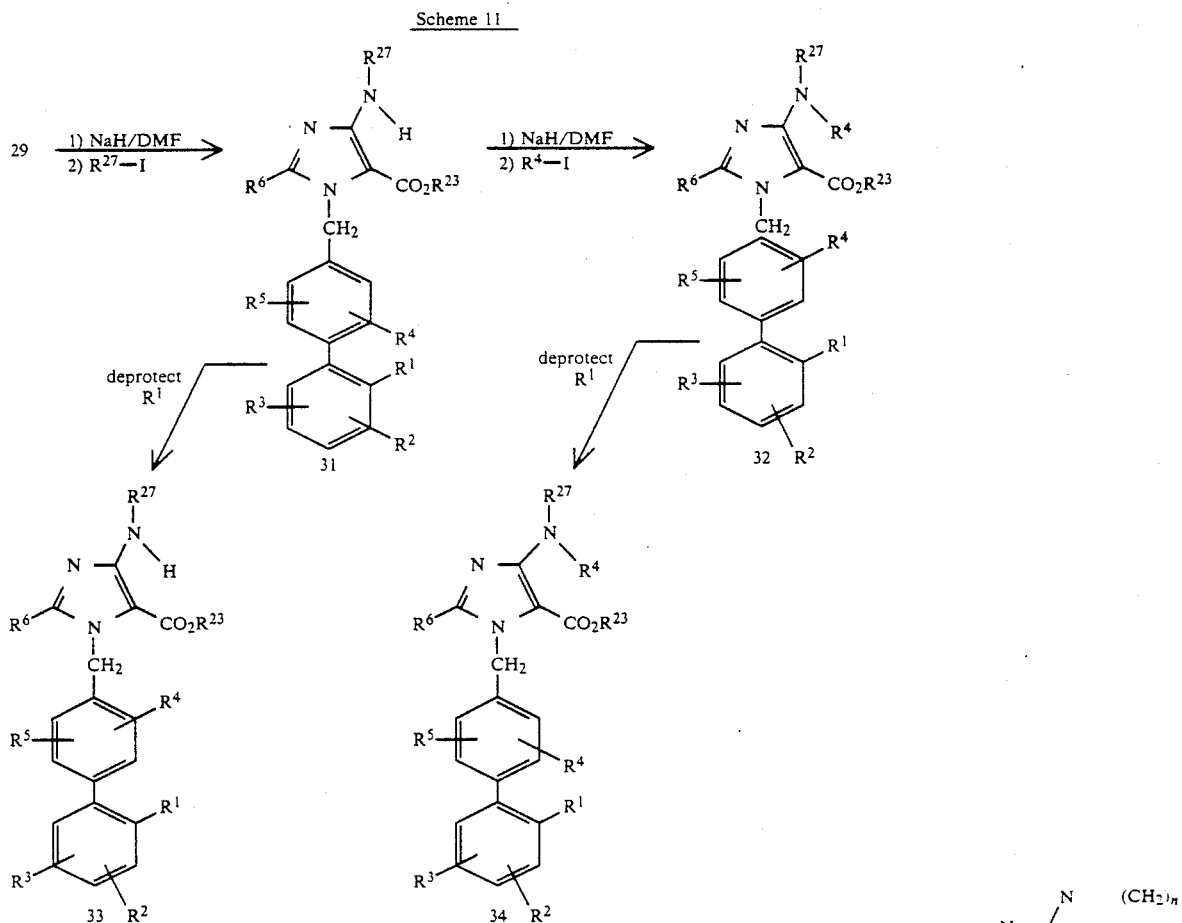

Alkylation of (29) with a bidentate alkylating agent, as shown in Scheme 12, leads to cyclization. Compound (35) is obtained after deprotection of $R^1$.

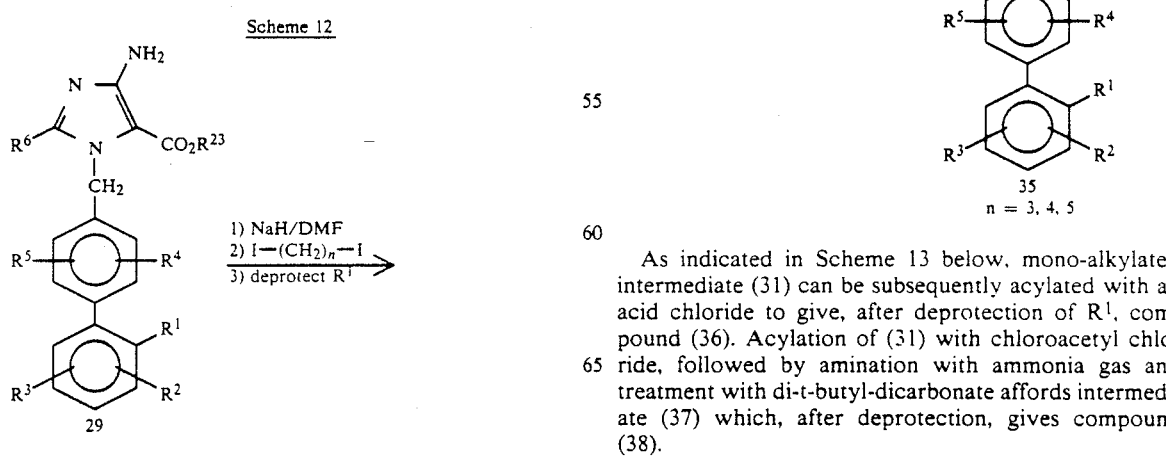

As indicated in Scheme 13 below, mono-alkylated intermediate (31) can be subsequently acylated with an acid chloride to give, after deprotection of $R^1$, compound (36). Acylation of (31) with chloroacetyl chloride, followed by amination with ammonia gas and treatment with di-t-butyl-dicarbonate affords intermediate (37) which, after deprotection, gives compound (38).

Scheme 13

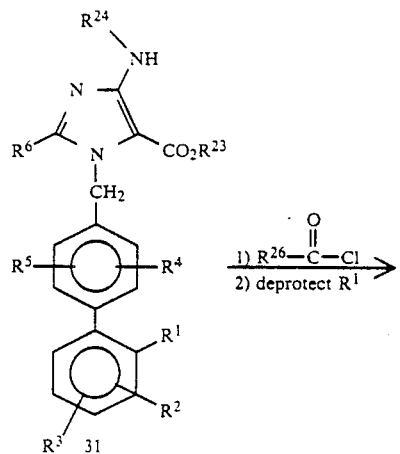

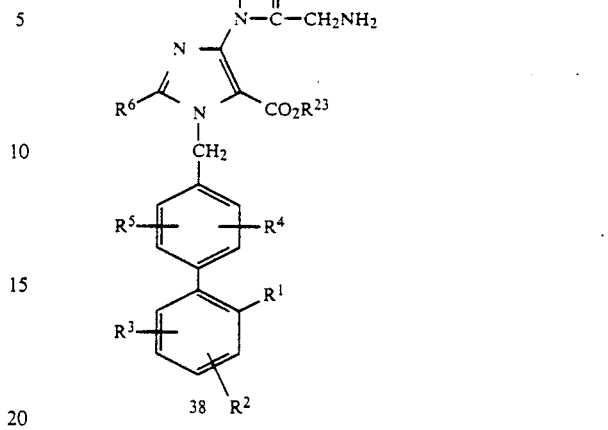

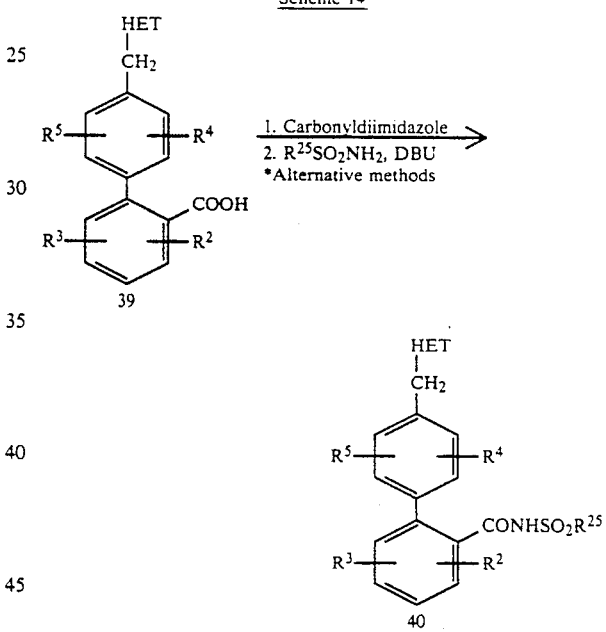

Scheme 14

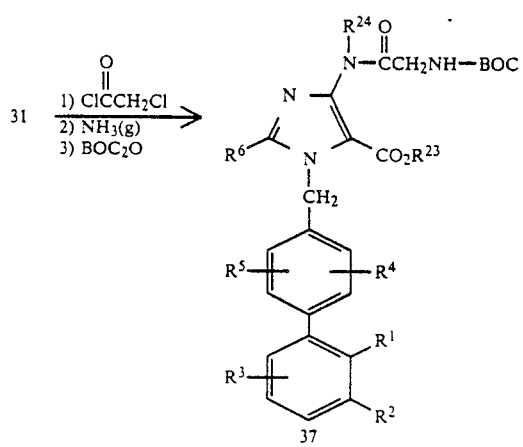

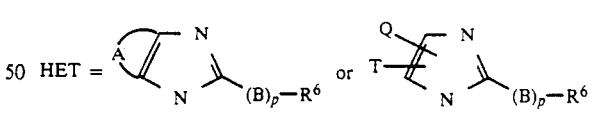

*Alternative Methods:
a) (i) SOCl₂, reflux (ii) R²⁵SO₂NH⁻M⁺ (where M is Na, K or Li)
b) (i) (COCl)₂—DMF, —20° C. (ii) R²⁵SO₂NH⁻M⁺
c) (i) N(N,N-Diphenylcarbamoyl)pyridinium chloride/Aq. NaOH (ii) R²⁵SO₂NH⁻M⁺

Compounds of formula I and formula Ia where $R^1$ is —CONHSO$_2$R$^{25}$ (where $R^{25}$ = alkyl, aryl or heteroaryl may be prepared from the corresponding carboxylic acid derivatives (39) as outlined in Scheme 14. The carboxylic acid (39), obtained as described earlier can be converted into the corresponding acid chloride by treatment with refluxing thionyl chloride or preferably with oxalylchloride and a catalytic amount of dimethylformamide at low temperature [A. W. Burgstahler, L. O. Weigel, and C. G. Shaefer-*Synthesis*, 767, (1976)]. The acid chloride then can be treated with the alkali metal salt of $R^{25}SO_2NH_2$ to form the desired acylsulfonamide 40. Alternatively, these acylsulfonamides may be also prepared from the carboxylic acids using N,N-diphenylcarbamoyl anhydride intermediates [F. J. Brown et al - *European Patent Application*. EP 199543; K. L. Shepard and W. Halczenko- *J. Het. Chem.*, 16, 321 (1979)]. Preferably the carboxylic acids (39) can be converted into acyl-imidazole intermediates, which can be then treated with an appropriate aryl or alkylsulfonamide and 1,8-diazabicyclo[5.4.o]undec-7 ene (DBU) to give the desired acylsulfonamide 40 [J. T. Drummond and G. Johnson—*Tetra. Lett.*—29, 1653 (1988)].

Chem. Soc., 66, (1944), 1459], or with dry powdered ammonium carbonate, E. H. Huntress and J. S. Autenrieth, J. Amer. Chem. Soc., 63, (1941), 3446; E. H. Huntress and F. H. Carten, J. Amer. Chem. Soc., 62, (1940), 511] to form the sulfonamide 42. The benzyl bromide 44 may be prepared from the sulfonamide 43b as outlined in Scheme 8, and then can be reacted with an alkali metal salt of an appropriate heterocyclic compound (HET) to form the key sulfonamide 45. The sulfonamide 45 may be also prepared from the aromatic sulfonyl chloride 50, which may be prepared (where applicable) from the aryl amine 49 as outlined in

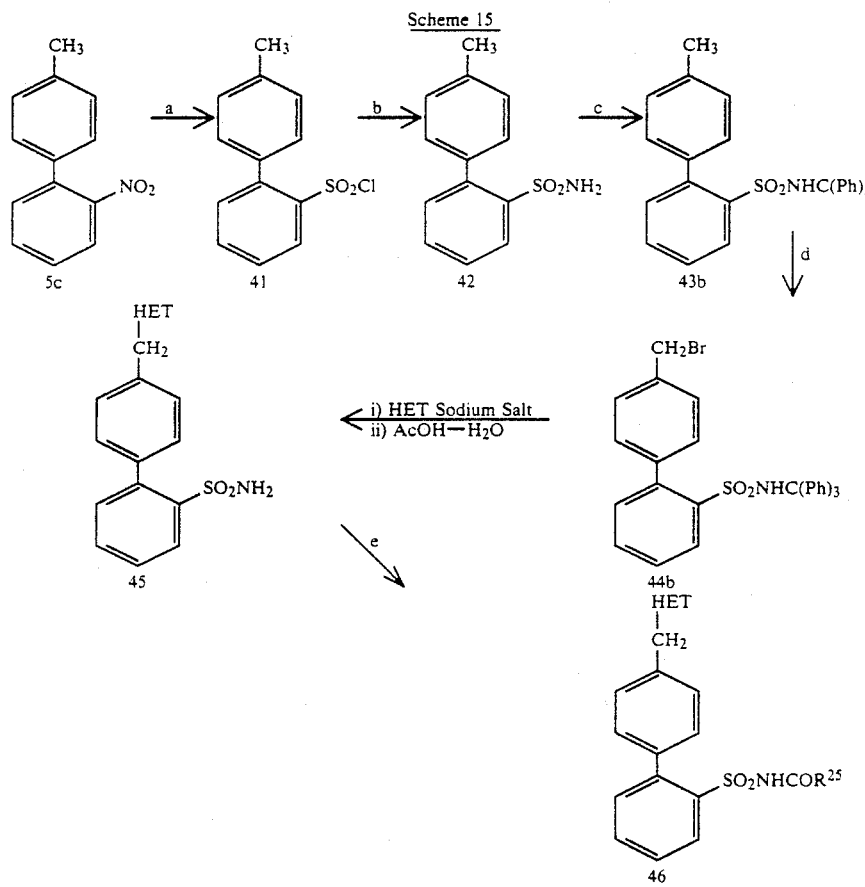

a. i) $H_2$/Pd—C, ii) $NaNO_2$—HCl, iii) $SO_2$, AcOH, $CuCl_2$
b. $NH_3$ or $(NH_4)_2CO_3$
c. $Ph_3CCl$, $Et_3N$, $CH_2Cl_2$, 25° C.
d. N-Bromosuccinimide
e. $R^{25}COCl$ or $R^{25}CO$—Im or other acylating agents
HET = same as in Scheme 14.

Compounds of formula I and formula Ia where $R^1$ is —$SO_2NHCOR^{25}$ may be prepared as outlined in Scheme 15. The nitro compound 5c (prepared as described in Scheme 2) can be reduced to the corresponding amino compound and converted into aromatic diazonium chloride salt, which then can be reacted with sulfur-dioxide in the presence of a copper (II) salt to form the corresponding arylsulfonylchloride 41 [H. Meerwein, G. Dittmar, R. Gollner, K. Hafner, F. Mesnsch and O. Steifor—*Chem. Ber.*, 90, 841 (1957); A. J. Prinsen and H. Cerfontain, Recueil, 84, 24 (1965); E. E. Gilbert, Synthesis, 3 (1969) and references cited therein]. The sulfonyl chloride thus obtained, can be reacted with ammonia in aqueous solution or in an inert organic solvent F. H. Bergheim and W. Baker, J. Amer.

Scheme 16. The acylation of 45 with appropriate acyl chlorides (or acyl-imidazoles of other acylating agents) may produce the desired acylsulfonamides 46.

Scheme 16

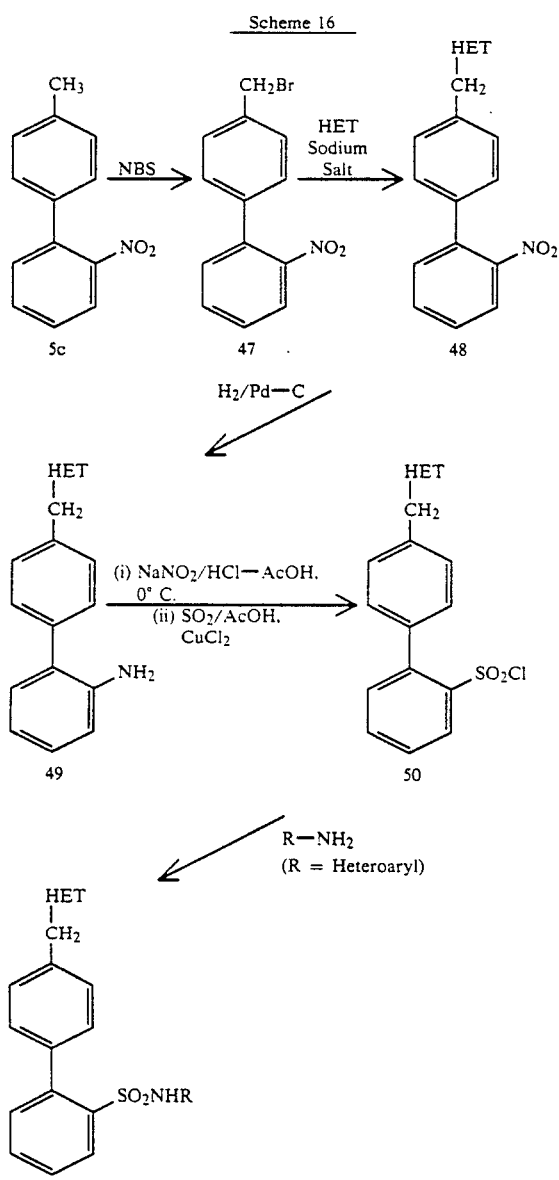

51
HET = same as in Scheme 14.

The compounds bearing $R^1$ as $-SO_2NHR^{25}$ (where $R^{25}$ is heteroaryl) may be prepared by reacting the aromatic sulfonyl chloride 50 with appropriate heteroaryl amines as outlined in Scheme 16. The sulfonyl chloride 50 may be the prefered intermediate for the synthesis of this glass of compounds. The aromatic sulfonyl chlorides may also be prepared by reacting the sodium salt of aromatic sulfonic acids with $PCl_5$ or $POCl_3$ [C. M. Suter, *The Organic Chemistry of Sulfur.* John Wiley & Sons, 459, (1944)]. The aromatic sulfonic precursors may be prepared by chlorosulfonation of the aromatic ring with chlorosulfonic acid [E. H. Huntress and F. H. Carten, *J. Amer. Chem. Soc.*, 511 (1940)].

The biaryl sulfonamide 43a and can be prepared alternatively using palladium(0) catalyzed cross-coupling reactions of appropriate aryl-organotin precursors [J. K. Stille, *Pure Appl. Chem.*, 1771 (1985); T. R. Baiely, *Tetra Lett.*, 27, 4407 (1986); D. A. Widdowson and Y. Z. Zhang, *Tetrahedron*, 42, 2111 (1986)], as outlined in Scheme 17. The organotin compound 53 [S. M. Moerlein, *J. Organometallic Chem.*, , 29 (1987), obtained from the aromatic precursce, may be coupled with aryl sulfonamide 55 or 56 using $Pd(PPh_3)_4$ or $(PPh_3)_2PdCl_2$ as catalysts to give biaryl sulfonamides 43a and 43b, respectively. Similarly, the benzyl bromide 44a and 44b may be alternatively prepared from the appropriate organotin precursor 59 using the Pd(0) catalyzed cross-coupling reaction as outlined in Scheme 18.

SCHEME 17

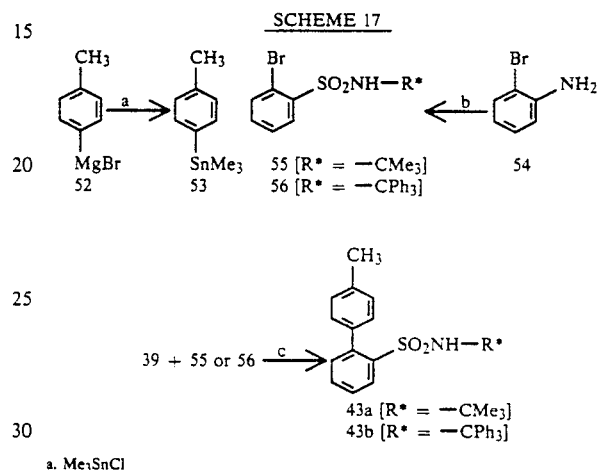

a. $Me_3SnCl$ b. (i) $NaNO_2/HCl$ (ii) $SO_2$, $CuCl_2$ (iii) t-Butylamine, or $NH_3$ and then $Ph_3CCl$ c. $Pd(PPh_3)_4$, Toluene or $(PPh_3)_2PdCl_2$, DMF, 90° C.

SCHEME 18

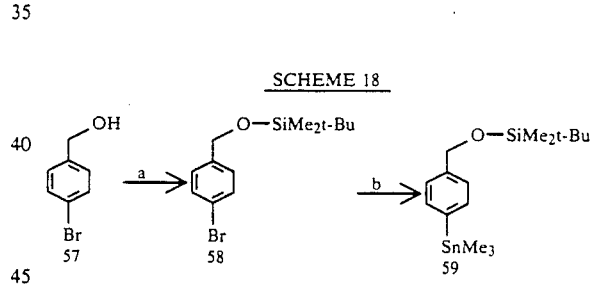

a. t-Bu $Me_2Si-Cl/Imidazole$, DMF b. t-BuLi, -78° C., $Me_3SnCl$ c. Tetrabutylammonium fluoride d. $CBr_4/Ph_3P$.

SCHEME 19

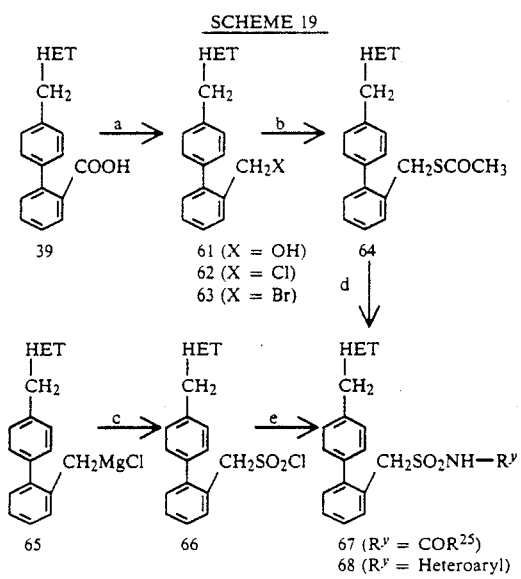

a. (i) EtOCOCl/Et₃N, THF, 0° C. (ii) NaBH₄ (iii) CCl₄ or CBr₄/PPh₃
b. AcSK
c. SO₂Cl₂
d. Cl₂, AcOH, H₂O or, (i) SO₂Cl₂ (ii) oxidation
e. R^yNH₂ or, (i) NH₃ (ii) Acylation.
HET = same as in Scheme 14.

The compounds of formula I and Ia bearing $R^1$ =—CH₂SO₂NHCOR²⁵ and —CH₂SO₂NHR²⁵ may be prepared as outlined in Scheme 19. The key precursor aryl-methanesulfonyl chloride 66 may be prepared either from the reaction of aryl-methylmagnesium chloride 65 (which may be obtained from the corresponding benzyl chloride 62) with sulfuryl chloride [S. N. Bhattacharya, C. Eaborn and D. P. M. Walton, *J. Chem. Soc. C*, 1265 (1968)], or by oxidation of the aryl-methylthioacetate 64 (may be prepared from the benzyl bromide 63 as outlined) with chlorine in presence of trace amount of water [Bagnay and Dransch, *Chem. Ber.*, 93, 784 (1960)]. Alternatively, the aryl-methylthioacetate 64 can be oxidized with sulfuryl chloride in presense of acetic anhydride to form aryl-methylsulfinyl chloride [S. Thea and G. Cevasco, *Tetra. Lett.*, 28, 5193 (1987)], which can be further oxidized with appropriate oxidizing agents to give the sulfonyl chloride 66. The compounds 67 and 68 can be obtained by reacting the sulfonyl chloride 66 with appropriate amines.

Compounds of formula I and Ia where $R^1$=—NHSO₂NHR²⁵ may be prepared by the reaction of appropriate primary amines with the sulfamide 71 [S. D. McDermott and W. J. Spillane, *Synthesis*, 192 (1983)], as described in Scheme 20. The compound 70 may be obtained from the corresponding N t-butylsulfamide 69 after treatment with anhydrous trifluoro-acetic acid [J. D. Catt and W. L. Matier, *J. Org. Chem.*, 39, 566 (1974)], which may be prepared by the reaction of the aromatic amine 49 with t-butylsulfamoyl chloride [W. L. Matier, W. T. Comer and D. Deitchman, *J. Med. Chem.*, 15, 538 (1972)].

SCHEME 20

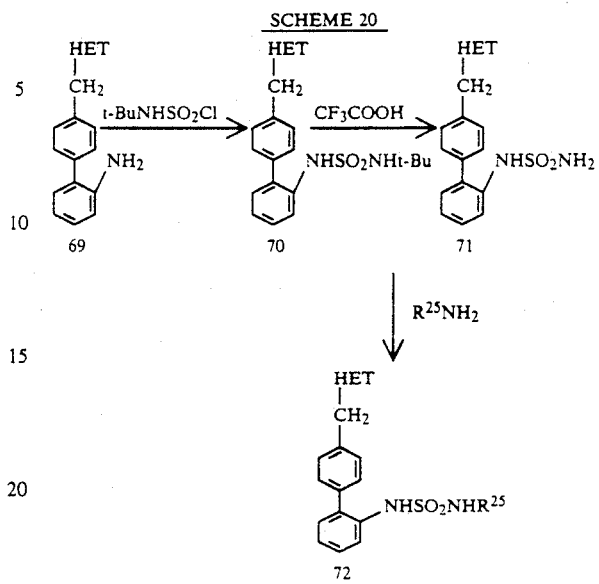

HET = same as in Scheme 14.

It will be appreciated by those skilled in the art that the protecting groups used in these syntheses will be chosen to be compatible with subsequent reaction conditions. Ultimately, they will be removed to generate the active compounds of formulae (I) and (Ia). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) were suspended in 5mM Tris-0 25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear](10ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonists which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10mM)-NaCl (120mM)-disodium EDTA (5mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10ml) and counted for radioactivity using Packard 2660 Tricarb liquid scintillation counter. The inhibitory concentration (IC$_{50}$) of potential AII antagonists which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below:

Male Charles River Sprague-Dawley rats (300-375 gm) were anesthetized with methohexital (Brevital; 50 mg/kg i.p. and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representive compounds of the invention were evaluated and all were found to exhibit an activity of at least IC$_{50}$<50 mM thereby demonstrating and confirming the utility of the compounds of the invention as effective AII antagonists.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenoolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis is necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or Formula Ia or a physiologically acceptable salt thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following a binder such as gum tragacanth, acacia, corn starch or gelatin; in excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, Sugar or both A syrup or elixir may contain the active compound sucrose as a sweetning agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formulas (I) and (Ia) and their incorporation into pharmaceutical compositions and as such are not to be considered as limiting the invention set forth in the claims appended hereto.

EXAMPLE 1

Preparation of
2-butyl-4-amino-5-carbomethoxy-1-[(2'-(tetrazol-5-yl)biphen-4-yl)methyl]imidaizole Step A: Preparation of ethyl valeramidate To 100 g (1.20mol) valeronitrile was added 71mL absolute ethanol (56 g 1.22 mol, 1.01 eq) and the mixture cooled to 0° under nitrogen. Dry hydrogen chloride gas was bubbled through the solution for one hour and then the mixture was allowed to warm to room temperature and stir overnight.

The mixture was stripped of all volatiles in vacuo at 40°; the residue slowly solidified to a pale yellow, low-melting solid. This solid was triturated with 500 mL of dry ether, filtered and washed with generous portions of dry ether. The titled compound was thus obtained as a hygroscopic white solid.

NMR 300MHz, CD$_3$OD): 1.02 (t,3H), 1.45 (m,2H), 1.53 (t,3H), 1.74 (m,2H), 2.69 (t,2H), 4.46 (q,2H).

Step B: Preparation of N-cyano-(ethylvaleramidate)

To a solution of 2.0g (12.1 mmol) of the product of Step 1(a) in 3mL absolute ethanol at room temperature was added 0.51g of cyanamide (12.1 mmol, 1.0 eq). After stirring overnight at room temperature, precipitated ammonium chloride was filtererd off and the filtrate stripped of solvent in vacuo. The residue was redissolved in ethyl acetate, filtered, and purified by medium pressure liquid chromatography on silica gel, eluting with ethyl acetate. In this manner, the titled compound was obtained as a colorless liquid.

NMR 200MHz, CDCl$_3$): 0.95 (t,3H), 1.35 (t,3H), 1.4 (m,2H), 1.68 (m,2H), 2.68 (t,2H), 4.30 (q,2H).

Step C: Preparation of N'-cyano-N-(carbomethoxy) methyl)valeramidate

To a solution of 1.474 mg (9.56 mmol) N-cyano(ethyl valeramidate) (Example 1, Step B) in 3 mL absolute methanol at room temperature was added 1.44 g (11.5 mmol, 1.2 eq methyl glycinate hydrochlroide followed by 6.67 mL triethylamine (4.84 g. 47.9 mmol, 5 eq). The mixture was stirred at room temperature overnight then filtered and the filtrate concentrated in vacuo to a gummy residue The residue was taken up in 50 mL of ethyl acetate and washed with 5% aqueous citric acid (2×) and brine (1×). The organic layer was removed, dried over magnesium sulfate, filtered and solvents removed in vacuo. The residue was purified by medium pressure liquid chromatography on silcia el, eluting with hexane/ethyl acetate (1:1). The title compound (0.998 g, 5.06 mmol, 53%) was thus obtained as a pale yellow oil that slowly solidified upon standing.

NMR (300 MHz. CDCl$_3$ 0.94 (t,3H). 1.41 (m,2H), 1.69 (m,2H), 2.62 (t,2H), 3.78 (s,3H), 4.06 (d,2H), 6.5 (br s, 1H).

EI-MS: 197 (+, 11%).

Step D: Preparation of 2-Cyano-4'-methyl-biphenyl

A solution of 4-bromotoluene (310 g, 1.81 moles) in 1500 ml of anhydrous ether was cooled to an internal temperature of −65° C. (slurry forms at ~−6° C.) under nitrogen. A solution of t-butyllithium (1.7 M in pentane, 2.2 L, 3.74 moles) was added over a period of ~90 minutes (internal temperature maintained below −55° C.). The cooling bath was then replaced with water baths which brought the reaction mixture up to +20° C. over 45 minutes and the white slurry was stirred an additional 2 hours at room temperature (most solids dissolved). The contents of this flask were then transferred under nitrogen pressure via a 1/8" plastic cannula to a stirred solution of ZnCl$_2$ in ether (1M, 1.86 L) and THF (3.7 L) over 25 minutes (a cool water bath was used to maintain an internal temperature of 25° C.). The reaction mixture was stirred at room temperature for 2 hours. The appearance may vary from a clear solution with white flocculent precipitate to a mixture with heavy white solids. The reaction mixture was then transferred via a 1/4" cannula under vacuum) to a solution of 2-bromobenzonitrile (220 g, 1.2 moles) and bis(triphenylphosphine) nickel (II) chloride (22 g, 0.0337 moles) in THF (3.1 L) at room temperature over 20 minutes. The internal temperature rose to 35° C. during additions but subsided when complete. The dark red solution was stirred at room temperature overnight. The reaction mixture was then added carefully in portions to ice cold 1N HCl (~15 L) stirred rapidly in a large extractor. The organic layer was separated and the aqueous phase extracted with ether (3×2 L). The organic layers were combined and washed with water (2×2 L), brine, dried over MgSO$_4$ and filtered through a plug of silica gel. The solution was concentrated to give the crude product as an oily solid (275 g). The material was then purified on a silica gel column (3 kg of E. Merck SiO$_2$60, 70-230 mesh) using methylene chloride-hexane (1:4) to give 196 g (85%) of the title compound as a low melting (46°-49.5° C.) solid. NMR (CDCl$_3$): 2.22 (s, 3H), 7.24-7.78 (8H).

Step E: Preparation of trimethylstannyl azide

To a concentrated solution of sodium azide (1.2 kg, 18.5 moles) in water (3 L), a solution (required a little warming) of trimethyltin chloride (600 g, 3 moles) in dioxane (400 ml) was added in three portions with vigorous stirring. The immediate formation of a white precipitate was observed and no exotherm was recorded. The mixture was stirred overnight at room temperature. The solids were filtered, washed with water, dried under suction in the funnel and then over P$_2$O$_5$ under vacuum. Yield 541 g (88%); mp 120°-122° C. The material was used without further purification.

Step F: Preparation of 5-(4'-methylbiphen-2-yl)-tetrazole

To a solution of 390 g (2.02 moles) 2-cyano-4'-methylbiphenyl (Example 1, Step D) in toluene (2.3 l was added trimethylstannyl azide (Example 1, Step E)(525g, 2.55 moles) at room temperature. The mixture was refluxed for 24 hours, cooled to room temperature, filtered, washed with toluene and sucked "dry" in a funnel. This gave the desired intermediate as a moist cake (1 kg). A small portion was dried further to give a white solid. mp 261°-266.5° C. (dec.) NMR (DMSO-d$_6$): 0.35 (s, 9H), 2.23 (s, 3H), 6.96 (dd, 4H), 7.44 (m, 4H).

The intermediate was re-suspended in toluene (3.5 L) and THF (250 ml) was added. Anhydrous HCl was bubbled in at a moderate rate at room temperature to give a clear solution (~45 minutes). Addition of HCl gas was continued for another 20 minutes with stirring whereupon a white precipitate appeared. The HCl bubbler was removed and the mixture stirred at room temperature overnight (convenient). The solid product was filtered, washed with toluene followed by ether and then dried under vacuum. This produced 250 g of the title compound. mp 152°-154C.; NMR (CDCl$_3$): 2.4 (s, 3H), 7.19 (dd, 4H), 7.4 (dd, 1H), 7.55 (m, 2H), 8.25 (dd, 1H). May be crystallized from toluene.

Step G: Preparation of N-triphenylmethyl-5-(4'-methylbiohen-2-yl)tetrazole

To a cloudy solution of 250 g (1.06 moles) of the product from Step F in methylene chloride (4 L) was added triphenylmethyl chloride (310 g, 1.11 moles) at room temperature. The reaction mixture was stirred and triethylamine (190 ml, 138 g, 1.36 moles) was added in portions. After addition, the mixture was stirred at reflux (~40° for 90 minutes. The solution was cooled to room temperature, washed with water 2×1 L), dried over MgSO$_4$, filtered through a silica gel plug and concentrated on the rotovap to a solid. This was crystallized from toluene to give the title compound as an off-white solid (425 g, 84%);mP 166°-168° C.;NMR (CDCl$_3$):2.28 (s,3H). 6.9-7.05 (m,~10H), 7.2-7.5 (m,~12H), 7.9 (dd,1H), Step H: Preparation of N-triphenylmethyl-5-(4'-bromomethylbiohen-2-yl)tetrazole To a solution of 425 g (0 89 moles) of N-triphenylmethyl-5-[2-(4'-methylbiphenylyl)]tetrazole in CCl$_4$ (4.0 L) were added freshly opened N-bromosuccinimide (159 g, 0.89 moles) and dibenzoyl peroxide (22 g, 0.089 moles). The mixture was refluxed for 2 hours, cooled to room temperature and filtered. The filtrate was concentrated in vacuo to give a thick oil. The addition of ether (~2.0 L) to this oil resulted in a clear solution followed by crystallization, filtration gave the title compound as a white solid (367 g, 74%). mp 137°-139.5° C.; NMR (CDCl$_3$):4.38(s.2H)'6.9-8.0(m.~23H). There is a trace of starting material still present.

Step I: Preparation of 4-amino-2 butyl 5 carbomethoxy-1-[(2'-(N-triphenylmethyltetrazol-5-yl)biphen-4-yl)methyl]imidazole To a solution of 137 mg (0.69 mmol) (N'-cyano-N-(carbomethoxy)methylvaleramidate (Step C) in 1 mL dry dimethyl formamide at room temperature was added 33 mg of sodium hydride (60% oil dispersion;

0.83 mmol, 1.2 eq). After 15 minutes, a solution of 386 mg (0.69 mmol, 1.0 eq) N-triphenylmethyl-5(4'-bromomethylbiphen-2-yl)tetrazole (Step H) was added and the mixture stirred at room temperature for 14 hours. The mixture was treated with one drop of glacial acetic acid then added to 30 mL ethyl acetate and washed once with 5% aqueous citric acid and once with brine. The organic layer was removed, dried over MgSO4, filtered and solvents removed in vacuo. The residue was purified by medium pressure liquid chromatography on silica gel, eluting with ethyl acetate to afford 172 mg (0.26 mmol, 37%) of the title compound as a pale yellow foam.

NMR (300 MHz, CDCl3): 0.83 (t,3H), 1.25(m,2H),1.58 (m,2H), 2.40 (t,2H), 3.67 (s,3H), 4.9 (br s, 2H), 5.29 (s,2H), 6.80 (d,2H), 6.90 (d,6H), 7.05 (d,2H), 7.2-7.5 (m,12H), 7.88 (d,1H).

FAB-MS: 674 (M+H, 8%), 243 (trityl+, 100%).

Step J: Preparation of 4-amino-2-butyl-5-carbomethoxy-1-(2'-(tetrazol-5-yl)biphen 4 yl)methylimidazole To a solution of 47 mg (0.070 mmol) 4-amino-2-butyl-5-carbomethoxy-1-(2'-(N-triphenylmethyltetrazol-5-yl)biphen-4-yl)methylimidazole (Example 1, Step I) in 1 mL glacial acetic acid was added 1 mL distilled water and the mixture stirred at room temperature for 14 hours. All volatiles were removed in vacuo and the residue purified by medium pressure liquid chromatography on silica, eluting with ethyl acetate/acetonitrile/methanol (9:1:.5), to afford 24 mg (0.056 mmol, 79%) of the title compound as a pale yellow powder.

NMR (300 MHz, CDl3OD): 0.92 (t,3H), 1.37 (m,2H), 1.58 (m,2H), 2.66 (t,2H), 3.77 (s,3H), 5.51 (s,2H), 7.03 (d,2H), 7.13 (d,2H), 7.6 (m,2H), 7.7 (m,2H).

FAB-MS: 432 (M+H,100%).

EXAMPLE 2

2-Butyl-5-carbomethoxy-4-(methylamino)-1-(2'(tetrazol-5-yl)biphen-4-yl)methylimidazole Step A: Preparation of 2-butyl-5-carbomethoxy-4(methyamino)-1-(2'-(N-triphenylmethyltetra-zol-5-yl)biphen-4-yl)methylimidazole and 2-butyl-5-carbomethoxy-4-(dimethylamino)-1-(2'-(N-triphenylmethyltetrazol-5-yl)biphen-4-yl)methylimidazole To a solution of 103 mg (0.15 mmol) 2-butyl-4-amino-5-carbomethoxy-1-(2'-(N-triphenylmethyltetra-zol-5-yl)-biphen-4-yl)methylimidazole (Example 1, Step I) in 1 mL dry DMF at room temperature was added 7 mg sodium hydride/oil dispersion (60% dispersion; 0.18 mmol, 1.1 eq). After 15 minutes at room temperature, two drops of methyl iodide were added and the mixture capped tightly and stirred at room temperature for 16 hours. Two drops of glacial acetic acid were added and the mixture diluted into 20 mL ethyl acetate and washed with pH 7.0 phosphate buffer (2×) and brine (1×). The organic layer was removed, dried over magnesium sulfate, filtered and stripped; the residue was purified by medium pressure liquid chromatography on silica, eluting with ethyl acetate/hexane (2:1) to afford 65 mg of a 2:1 mixture of mono- and di-methylated products in addition to 23 mg of recovered starting material.

Step B: Preparation of 2-butyl-5-carbomethoxy-4-(methylamino)-1-(2'-tetrazol-5-yl)biphenyl]-4-yl)methylimidazole and 2-butyl-5-carbomethoxy-4-(dimethylamino)-1-(2'-(tetrazol-5-yl)biphen-4-yl)methylimidazole 65 mg of the mixture of intermediates described in Step A above was dissolved in 2 mL glacial acetic acid and treated with 2 mL distilled water for 18 hours at room temperature. All volatiles were removed in vacuo and the residue purified by reverse phase HPLC on C18 eluting with methanol/0.1% aqueous trifluoroacetic acid (gradient: 65% MeOH to 75% MeOH linearly over 10 minutes). In this manner, 27 mg 0.061 mmol'40%) of the title compound, 2-butyl-5-carbomethoxy-4-(methylamino)-1-(2'-(tetrazol-5-yl)biphen-4-yl)methylimidazole in addition to 12 mg of the dimethyl compound (Example 3) were isolated.

NMR (300 MHz, CD3OD): 0.94 (t,3H), 1.41 (m,2H), 1.46 (m,2H), 2.92 (t,2H), 3.08 (s,3H), 3.81 (s,3H), 5.72 (s,2H), 7.16 (m,4H), 7.6 7.8 (m,4H).

FAB-MS: 446 (M+H,100%)

EXAMPLE 3

2-Butyl-5-carbomethoxy-4-(dimethylamino)-1-(2'-tetrazol-5-yl)biphen-4yl)methylimidazole As described in Example 2 Step B), 12 mg (0.026 mmol, 17%) of the title compound was obtained from HPLC separation of a mixture of mono and dimethylated compounds.

NMR (300 MHz, CD3OD): 0.95 (t,3H), 1.42 (m,2H), 1.60 (m,2H), 2.92 (t,2H), 3.12 (s,6H), 3.80 (s,3H), 5.70 (s,2H), 7.11 (d,2H), 7.18 (d,2H), 7.55-7.75 (m,4H).

FAB-MS: 460 (M+H,100%).

EXAMPLE 4

2-Butyl-5-carbomethoxy 4-(pyrrolidin 1-yl) 1 (2'-(tetrazol-5-yl-binpen-4-yl)methylimidazole Step A: Preparation of 2-butyl-5-carbomethoxy-4-(pyrrolidin-1-yl)-1-(2'-(N-triphenylmethyl-tetrazol-5-yl-biphen-4-yl)methylimidazole To a solution of 65 mg (0 096 mmol) 4-amino-2-butyl-5-carbomethoxy-1-(2'-(N-triphenylmethyl-tetrazol-5-yl)biphen-4-yl)methylimidazole (Example 1, Step I) in 0.25 mL dry DMF at room temperature was added 9 mg of sodium hydride/oil dispersion (60% dispersion. 0.23 mmol. 2.3 eq). After 15 minutes at room temperature. 20 uL of 1,4-dibromobutane was added and the mixture stirred at room temperature for three days. The mixture was diluted with 10 mL ethyl acetate and washed with pH 7.0 phosphate buffer and brine. The organic layer was removed, dried (MgSO4), filtered and solvents removed in vacuo. The residue was purified by medium pressure liquid chromatography on silica, eluting with ethyl acetate/hexanes (2:1) to afford 42 mg (0.058 mmol, 60%) of the title compound as a colorless oil.

NMR (300 MHz, CDCl3): 0.82 (t,3H), 1.25 (m.2H), 1.55 (m,2H), 1.88 (m,4H), 2.46 (t,2H), 3.46 (m,4H), 3.60 (s,3H), 5.32 (s,2H), 6.77 (d,2H), 6.91 (d,6H), 7.04 (d,2H), 7.2-7.5 (m,12H), 7.85 (d,1H).

Step B: Preparation of 2-butyl 5-carbomethoxy-4-(pyrrolidin-1-yl) 1-(2'(tetrazol-5-yl)-biphen-4-yl)methylimidazole The intermediate described in Step A above (42 mg, 0.058 mmol) was dissolved in 0.5 mL glacial acetic acid and treated with 0.5 mL water for 12 hours at room temperature. All volatiles were removed in vacuo and the residue purified by medium pressure liquid chromatography on silica, eluting with ethyl acetate/acetonitrile/methanol (9:1:.25) to afford 23 mg (0.047 mmol, 49% overall) of the title compound as a pale yellow solid.

NMR (300 MHz, $CDl_3OD$): 0.92 (t,3H), 1.39 (m,2H), 1.57 (m,2H), 1.95 (m,4H), 2.70 (t,2H), 3.46 (m,4H), 3.65 (s,3H), 5.52 (s,2H), 7.00 (d,2H), 7.12 (d,2H), 7.55-7.70 (m,4H).

FAB-MS: 486 (M+H,100%).

EXAMPLE 5

4-Acetamido-2-butyl-5-carbomethoxy-1-(2'-(tetrazol-5-yl)biphen-biphen-4-yl)methylimidazole Step A: Preparation of 4-acetamido-2-butyl-5-carbomethoxy-1-(2'-(N-triphenylmethyltetrazol-5yl)biphen-4-yl)methylimidazole To a solution of 86 mg (0.13 mmol) of the intermediate described in Example 1 (Step I) in 2 mL methylene chloride at 0° under nitrogen was added 110 uL of diisopropylethyl amine (82 mg, 0.63 mmol, 5 eq) followed by 14 uL of acetyl chloride (15 m . 0.20 mmol, 1.5 eq . The mixture was stirred at 0° for one hour then allowed to warm to room temperature slowly. The mixture was diluted with 5 mL ethyl acetate and washed once with 5% aqueous citric acid and once with brine. The organic layer was removed, dried over magnesium sulfate, filtered and solvent removed. The residue was purified by medium pressure liquid chromatography on silica, eluting with ethyl acetate to afford 72 mg (0.10 mmol, 79%) of the title compound as a colorless oil.

NMR (300 MHz, CDC13): 0.83 (t,3H), 1.24 (m,2H), 1.63 (m,2H), 2.20 (s,3H), 2.52 (t,2H), 3.66 (s,3H), 5.46 (s,2H), 6.76 (d,2H), 6.92 (d,6H), 7.08 (d,2H), 7.2-7.4 (m,10H), 7.45 (m,2H), 7.88 (m,1H).

Step B: Preparation of 4-acetamido-2-butyl-5-carbomethoxy-1-(2'-(tetrazol-5-yl)biphen-4-yl) methylimidazole 65 mg (0.09 mmol) of the intermediate described in Step A above was dissolved in 0.5 mL glacial acetic acid and treated with 0.5 mL distilled water for fourteen hours. All volatiles were removed in vacuo and the residue purified by medium pressure liquid chromatography on silica, eluting with ethyl acetate/acetonitrile/ methanol (9:1:0.25) to afford 32 mg 0.068 mmol, 74%) of the title compound as a white powder. NMR (300 MHz, $CDCl_3$): 0.88 (t,3H), 1.32 (m,2H), 1.68 (m,2H), 2.26 (s,3H), 2.62 (t,2H), 3.71 (s,3H), 5.05 (s,2H), 6.95 (d,2H), 7.11 (d,2H), 7.39 (d,1H), 7.55 (m,2H), 7.98 (d,1H).

FAB-MS: 474 (M+H,28%)

EXAMPLE 6

4-Acetoxyacetamido-2-butyl 5-carbomethoxy-1-(2'-(tetrazol-5-yl)biphen-4-yl)methylimidazole Step A: Preparation of 4-acetoxyacetamido-2-butyl-5-carbomethoxy-1-(2'-(N triphenylmethyl-tetrazol-5-yl)bipen-4-yl)methylimidazole To a solution of 110 mg (0.16 mmol) of the intermediate described in Example 1 (Step I) in 1 mL methylene chloride at 0 under nitrogen was added 85 uL of diisopropylethyl amine (63 mg, 0.49 mmol, 3 eq) followed by 26 uL of acetoxyacetyl chloride (33 mg, 0.24 mmol, 1.5 eq). The mixture was stirred at 0° for one hour then diluted with 10 mL ethyl acetate and washed once with 5% aqueous citric acid and once with brine. The organic layer was removed, dried over magnesium sulfate, filtered and solvent removed in vacuo. The residue was purified by medium pressure liquid chromatography on silica, eluting with ethyl acetate/hexane (2:1) to afford 115 mg (0.15 mmol, 91%) of the title Compound as a colorless glass.

NMR (300MHz, $CDCl_3$): 0.84 (t,3H), 1.29 (m,2H), 1.64 (m,2H), 2.23 (s,3H), 2.55 (br t,2H), 3.69 (s,3H), 4.8 (br s, 2H), 5.35 (s,2H), 6.76 (d,2H), 6.93 (d,6H), 7.09 (d,2H), 7.2-7.4 (m,10H), 7.47 (m,2H), 7.89 (m,1H).

FAB-MS: 773 (M+, 6%), 243 (Tr+, 100%).

Step B: Preparation of 4-acetoxyacetamido-2-butyl-5-carbomethoxy-1-(2'-(tetrazol-5-yl)biphen 4-yl)methylimidazole 110 mg (0.14 mmol) of the intermediate described in Step A above was dissolved in 1 mL glacial acetic acid at room temperature and treated with 1 mL distilled water for fourteen hours. All volatiles were removed in vacuo and the residue purified by medium pressure liquid chromatography on silica, eluting with ethyl acetate/acetonitrile/methanol (9:1:0.25) to afford 62 mg (0.12 mmol, 82%) of the title compound as a colorless glass.

NMR (300MHz, $CDCl_3$: 0.80 (br t,3H), 1.25 (br m,2H), 1.54 (br m,2H), 2.20 (s,3H), 2.46 (br m,2H), 3.73 (s,3H), 4.55 (br s,2H), 5.38 (s,2H), 6.84 (d,2H), 7.09 (d,2H), 7.37 (d,1H), 7.50 (m,2H), 7.85 (d,1H).

FAB-MS: 532 (M+H,100%)

EXAMPLE 7

4-(Aminoacetyl)amino-2-butyl-5-carbomethoxy-1-(2'-(tetrazol-5-yl)biphen-4-yl)methylimidazole Step A: Preparation of 2-butyl-4-chloroacetamido 5-carbomethoxy-1-(2'-(N-triphenylmethyl-tetrazol-5-yl)biphen-4-yl)methylimidazole To a solution of 142 mg (0.21 mmol) of the intermediate described in Example 1 (Step I) in 2 mL methylene chloride at 0° under nitrogen was added 60 uL of triethyl amine (44 mg, 0.43 mmol, 2 eq) followed by 20 uL of chloroacetyl chloride (28 mg, 0.25 mmol, 1.2 eq . The mixture was stirred at 0° for one hour then warmed to room temperature and stirred an additional hour. The mixture was diluted with 30 mL ethyl acetate and washed with 5% aqueous citric acid (2×) and brine (1×). The organic layer was removed, dried over magnesium sulfate, filtered and solvent removed. The residue was purified by medium pressure liquid chromatography on silica, eluting with ethyl acetate/hexanes (2:1)

to afford 129 mg (0.17 mmol, 82%) of the title compound as a white, crusty foam.

NMR 300MHz, DMSO-$d_6$): 0.76 (t,3H), 1.18 (m,2H), 1.48 (m,2H), 2.45 (s,3H), 3.61 (s,3H), 4.30 (s, 2H), 5.48 (s,2H), 6.9 (m,8H), 7.05 (d,2H), 7.3–7.6 (m,12H), 7.79 (d,1H).

FAB-MS: 750 (M+H,5%), 243 (Tr+, 100%).

Sep B: Preparation of 4-(t-butoxycarbonylamino) acetyl-2-butyl-5-carbomethoxy-1-(2'(N-tri-phenylmethyltetrazol-5-yl)biphen-4-yl) methylimidazole Ammonia was slowly bubbled through a solution of 82 mg (0.11 mmol) of the intermediate described in Step A above in 2 mL dry DMF at 60° for three hours. All volatiles were removed in vacuo, the residue re-dissolved in 2 mL methylene chloride and treated with excess (ca. 0.5 mL) di-t-butyl-dicarbonate. After 30 minutes at room temperature, all volatiles were removed in vacuo and the gummy residue extracted with several small portions of ethyl acetate. The combined extracts were concentrated to dryness and purified by medium pressure liquid chromatography on silica, eluting with ethyl acetate/hexanes (2:1) to afford 72 mg (0.087 mmol, 79%) of the title compound as a white foam.

NMR 300MHz, CDCl$_3$): 0.83 (t,3H), 1.26 (m,2H), 1.46 s'9H), 1.62 (m,2H), 2.52 (t,2H), 3.69 (s'3H), 5.34 s,2H), 6.75 d.2H), 6.91 (d.6H), 7.07 (d,2H), 7.2–7.5 (m,12H), 7 88 (d,1H),

FAB-MS: 831 (M+H,38%)

Step C: Preparation of 4-(aminoacetyl)amino-2-butyl-5-carbomethoxy-1-(2'-(tetrazol-5 yl)biphen-4-yl)methylimidazole To a solution of 70 mg (0.084 mmol) of the intermediate described in Step B above in 1 mL glacial acetic acid at room temperature was added 0.5 mL 6N HCl and the mixture stirred for two days. All volatiles were removed in vacuo and the residue purified by reverse phase HPLC on C-18, eluting with methanol/0.1% aqueous trifluoroacetic acid (gradient: 70% methanol increased linearly to 80% methanol over ten minutes). The title compound, as its trifluoroacetate salt (46 mg, 0.076 mmol, 91%) was thus obtained as a white powder.

NMR (300MHz, CD$_3$OD): 0.95 (t,3H), 1.30 (m,2H), 1.65 (m,2H), 2.78 (m,2H), 3.83 (s,3H), 4.1 (br s,2H), 5.66 (s,2H), 7.05 (d,2H), 7.16 (d,2H), 7.6–7.8 (m,4H).

FAB-MS: 489 (M+H,100%).

EXAMPLE 8

2-Butyl-4-[N-methyl N-[(benzyloxycarbonyl)acetyl]] amino-5-carbomethoxy-1-((tetrazol-5-yl)biphen-4-yl) methylimidazole Step A: Preparation of 2-butyl-4-(methylamino) 5-carbomethoxy-1-(2'-(N-triphenylmethyl) tetrazol-5-yl)biphen-4-yl)methylimidazole To a solution of 217 mg (0.322 mmol) 4-amino-2-butyl-5-carbomethoxy-1-((2'(N-triphenylmethyl)tetrazol-5-yl)biphen-4-yl) (Example 1, Step I) in 2 mL dry dimethylformamide at room temperature under nitrogen was added 17 mg of 60% sodium hydride/oil dispersion (10 mg NaH, 0.43mmol, 1.3 eq). After 15 minutes at room temperature, two drops of methyl iodide were added; the flask was stoppered tightly and the mixture stirred overnight.

The mixture was added to 50 mL ethyl acetate nd washed once with pH 7 phosphate buffer and once with brine. The organic layer was removed, dried over magnesium sulfate, filtered and solvents removed in vacuo. The residue was purified by medium pressure liquid chromatography on silica gel, eluting with ethyl acetate/hexane (2:1) to afford 180 mg (0.262 mmol, 81%) of the title compound which was contaminated with approximately 15% of dimethylated material.

NMR (200MHz, CDCl$_3$: 0.83 (t,3H), 1.22 (m,2H), 1.58 (m,2H), 2.46 (t,2H), 3.06 (d,3H), 3.63 (s,3H), 5.29 (s,2H), 5.5 (br s,1H), 6.78 (d,2H), 6.92 (d,6H), 7.15 (d,2H), 7.2–7.5 (m,12H), 7.88 (m,1H).

Step B: Preparation of 2-butyl-4-[N methyl-N-[(benzyloxycarbonylamino)acetyl]]amino-5carbomethoxy-1-[(2'-(N-triphenylmethyl)tetrazol-zol-5-yl)biphen-4-yl]methylimidazole 370 mg (1.77 mmol, 10 eq.) of N-carbobenzyloxy glycine was dissolved in 2mL dry methylene chloride at 0° under nitrogen and treated with 184 mg (0.89 mmol, 5 eq.) dicyclohexylcarbodiimide. The mixture was stirred at 0° for 30 minutes then a solution of 123 mg (0.18 mmol, 1.0 eq.) of the product of Step A in 1 mL methylene chloride was added and the mixture allowed to warm to room temperature and stir overnight.

The mixture was added to 50 mL ethyl acetate, filtered and the filtrate washed twice with saturated aqueous sodium bicarbonate and once with brine. The organic layer was removed, dried over magnesium sulfate, filtered and solvents removed in vacuo. The residue was purified by medium pressure liquid chromatography on silica gel, eluting with ethyl acetate/hexane (2:1) to afford 180 mg (0.262 mmol, 81%) of the title compound which was contaminated with approximately 15% of dimethylated material.

NMR (200 MHz, CDCl$_3$0.83 (t,3H), 1.22 (m,2H). 1.58 (m,2H), 2.46 (t,2H), 3.06 (d,3H), 3.63 (s,3H). 5.29 (s,2H), 5.5 (br s,1H), 6.78 (d,2H). 6.92 (d,6H), 7.15 (d,2H), 7.2–7.5 (m,12H), 7.88 (m,1H).

Step C: Preparation of 2-butyl-4-[N methyl-N [(benzyloxycarbonylamino)acetyl]]amino-5-carbomethoxy-1-(2'-(tetrazol 5-yl)biphen-4 yl)-methylimidazole 124 mg (0.14 mmol) of the product of Step B in 4 mL glacial acetic acid was treated with 4 mL distilled water and the resulting mixture stirred 18 hours at room temperature.

All volatiles were removed in vacuo and the residue purified by medium pressure liquid chromatography on silica gel, eluting with ethyl acetate/acetonitrile/methanol (9:1:0.5)) to afford 85 mg (0.13 mmol, 95%) of the title compound as a pale yellow foam.

NMR (200MHz, CDCl$_3$: 0.94 (t,3H), 1.42 (m,2H), 1.78 (m,2H), 2.81 (t,2H), 3.21 (s,3H), 3.68 (d,2H), 3.73 (s,3H), 4.88 (s,2H), 5.46 (s,2H), 5.76 (br t,1H), 6.92 (d,2H), 7.0–7.6 (m,10H), 7.86 (d,1H).

FAB-MS: 637 (M+H,100%).

EXAMPLE 9

2-Butyl-4-[N-methyl-N-aminoacetyl]amino-5-carbomethoxy-1-(2'-(tetrazol-5-yl)biphen-4-yl)methylimidazole A solution of 72 mg (0.11 mmol) of the compound described in Example 8 (Step C) was dissolved in 2 mL methanol and hydrogenated at 1 atmosphere over 15 mg of 10% Pd(OH)$_2$/C for one hour. The reaction mixture was filtered through Celite and solvent removed under vacuum to afford 55 mg (0.10 mmol, 91%) of the title compound as a colorless glass.

NMR (200MHz, CD$_3$OD): 0.88 (t,3H), 1.34 (m,2H), 1.62 (m,2H), 2.72 (t,2H), 3.20 (s,3H), 3.52 (s,2H), 3.76 (s,3H), 5.60 (s,2H), 6.98 (d,2H), 7.08 (d,2H), 7.52 (m,2H), 7.60 (m,2H).

FAB-MS: 503 (M+H,100%).

EXAMPLE 10

2-Butyl-4-methyl-1-(2'-(tetrazol-5-yl)biphen-4-yl) methyl-1,4,6,7-tetrahydroimidazo[4,5-e]-[1,4]-diazepine-5,8-dione A solution of 50 mg (0.099 mmol) of the compound described in Example 9 dissolved in 5 mL dry DMF was treated with 5 mg (0.04 mmol, 0.4 eq) 4-(dimethylamino)pyridine and the resulting solution heated at 140° under nitrogen for one hour. All volatiles were removed under vacuum nd the residue purified by reverse phase HPLC on C-18 eluting with methanol/0.1% aqueous trifluoroacetic acid (gradient: 75% methanol to 85% methanol linearly over ten minutes). In this manner, 19 mg (0.040 mmol, 41%) of the title compound was obtained as a colorless glass. In addition, 25 mg (0.047 mmol, 47%) of the more mobile N-formyl derivative of the starting material was obtained as a by-product.

NMR (200MHz, CD$_3$OD): 0.87 (t,3H), 1.34 (m,2H), 1.58 (m,2H), 2.66 (t,2H), 3.39 (s,3H), 3.80 (s,2H), 5.55 (s,2H), 7.05 (s,4H), 7.5-7.7 (m,4H).

FAB-MS: 471 (M+H,60%).

EXAMPLE 11

2-Butyl-4-[N-methyl-N-[N'-formyl]aminoacetyl]amino-5-carbomethoxy-1-((tetrazol-5-yl)biphen-4-yl)methylimidazole The title compound was isolated as a colorless glass as described in Example 10.

NMR (200MHz, CD$_3$OD): 0.87 (t,3H), 1.33 (m,2H), 1.60 (m,2H), 2.69 (t,2H), 3 18 (s,3H), 3.73 (s,3H), 3 85 s,2H), 5.53 (s,2H), 7.00 (d,2H), 7.11 (d,2H), 7.5-7.7 (m,4H), 8.07 (br s,1H).

FAB-MS: 531 (M+H,100%).

EXAMPLE 12

4-Amino-2-butyl-5-carboethoxy-1 (2'carboxybiphen-4-yl)methylimidazole

Step A: Preparation of N'-cyano-N-[(carboethoxy) methyl]-valeramidine

To a solution of 100 mg (0.65 mmol) N-cyano-(ethyl-valeramidate) (Example 1, Step B, in 2 mL absolute ethanol at room temperature was added 100 mg (0.72 mmol, 1.1 leq) ethyl glycinate hydrochloride followed by 0.30 mL triethylamine (220 mg, 2.16 mmol, 3.3 eq). The mixture was stirred at room temperature overnight then concentrated in vacuo to a gummy residue. The residue was treated with 20 mL of hexane/ethyl acetate (1:1), stirred vigorously, filtered, and the filtrate purified by medium pressure liquid chromatography on silica gel, eluting with hexane/ethyl acetate (1:1). The title compound (119 mg, 0.56 mmol, 87%) was thus obtained as a pale yellow oil that slowly solidified upon standing.

NMR(200MHz,CDCl$_3$): 0.95(t,3H),1.28(t,3H),1.42(m,2H),1.72(m,2H),2.65 (t,2H),4.05(d,2H),4.25(q,2H),6.7(br s,1H).

B: Preparation of N'-Cyano-N-(carboethoxymethyl)-N-(2'-t-butoxycarbonylbiphen 4-yl) methylvaleramidine To a solution of 119 mg (0.56 mmol of the product of Step A in 1 mL dry DMF at room temperature (under N$_2$) was added 23 mg of 60% sodium hydride-oil dispersion (14 mg NaH, 0.58 mmol, 1.05 eq). After 15min., a solution of 195 mg (.56 mmol, 1.0 eq) 4'-bromomethyl-2-t-butoxycarbonylbiphenyl in 1 mL dry DMF was added and the mixture stirred at room temperature for 6 hours. [The bromide was synthesized by the method of Carini, et al, European Patent Application 253,310 (to DuPont), 1988.]

The mixture was diluted with 30 mL ethyl acetate, washed twice with 5% aqueous citric acid, twice with 5% aqueous sodium bicarbonate and once with brine. The organic layer was separated, dried over MgSO$_4$, filtered and stripped of solvent in vacuo. The crude product was purified by medium pressure liquid chromatography on silica gel, eluting with hexane/ethyl acetate (2:1) to afford the title compound as a colorless oil.

NMR (300MHz, CDCl$_3$: The $^1$H NMR spectrum indicates that the product exists as a mixture of rotamers in a ratio of approximately 80:20. 0.95 (t,3H), 1.25 (t,3H), 1.28 (s,9H), 1.48 (m,2H), 1.74 (m,2H), 2.70 (t,.2×3H), 2.82 (t,.8×3H)], [4.02 (s,2×2H), 4.10 (s,.8×2H)], 4.2 (q,2H), [4.70 (s,8×2H), 4.80 (s,.2×2H), 7.1-7.8 (m,8H).

Step C: Preparation of 4 amino-2-butyl-5 carboethoxy-1-(2'-t-butoxycarbonylbiphen-4-yl) methylimidazole To a solution of 98 mg (0.21 mmol) of the product of Step B in 2 mL absolute ethanol at room temperature was added a solution made from 3 mg of sodium hydride (60% oil dispersion; 0.07 mmol, 0.3 eq) in 1 mL absolute ethanol. The mixture was stirred at room temperature for 3 hours then treated with several drops of glacial acetic acid. The mixture was added to 30 mL ethyl acetate and washed once with saturated aqueous sodium bicarbonate and once with brine. The organic layer was separated, dried over MgSO$_4$, filtered and solvents removed in vacuo. The residue was purified by medium pressure liquid chromatography on silica gel, eluting with ethyl acetate to afford the title compound as a pale yellow oil.

NMR (300MHz, CDCl$_3$): 0.85 (t,3H)'1.20 (s,9H)'1.26 (t'3H)'1.32 (m'2H), 2.59 (t,2H), 4.20 (q'2H), 5.0 (variable, br s.1H), 5.46 (s'2H)'7.03 (d,2H), 7.25 (m,3H), 7.36 (t,1H), 7.45 (t,1H), 7.75 (d,1H).

Step D: 4-Amino-2-butyl-5-carboethoxy-1-(2'-carboxy-biphen-4-yl)methylimidazol

To a solution of 32 mg (0.067 mmol of the intermediate described in Step C in 1 mL methylene chloride at room temperature was added several drops of anisole followed by 1 mL anhydrous trifluroacetic acid. After 3 hours, all volatiles were removed in vacuo and the residue Purified by reverse phase HPLC on C18 eluting with methanol/0.1% aqueous trifluoroacetic acid (linear gradient: 70% methanol to 80% methanol over 10 minutes). The title compound (22 mg, 0.052 mmol, 78%) was thus obtained as a light yellow powder.

NMR (300MHz, CD$_3$OD): 0.94 (t,3H), 1.30 (t,3H), 1.40 (m,2H). 1.61 (m,2H). 2.94 (t,2H). 4.35 (q,2H), 5.76

(s'2H). 7.22 (d,2H). 7.38 (m.3H). 7.47 (t,1H)'7.59 (t,1H). 7.86 (d.1H).
FAB-MS: 422 (M+H, 100%).

EXAMPLE 13

2-Butyl-4-methylamino-5-carboethoxy-1-(2-carboxybiphen-4-yl)methylimidazole

Step A: Preparation of 2-butyl-4-methylamino-5-carboethoxy-1-(2'-t-butoxycarbonylbiphen-4-yl)methylimidazole and 2 butyl 4-dimethyl-amino-5-carboethoxy-1-(2'-t-butoxycarbonyl-biphen-4-yl)methylimidazole To a solution of 92 mg (0.19 mmol) of the intermediate described in Example 12 (Step C) in 1 mL dry dimethyl formamide at room temperature was added 9 mg of sodium hydride oil dispersion (60% dispersion; 5.4 mg NaH, 0.23 mmol, 1.2 eq). After 30 minutes, a solution of two drops (excess) methyl iodide in 0.5 mL DMF was added and the mixture stirred at room temperature overnight. The mixture was added to 20 mL ethyl acetate and washed with 5% aqueous citric acid and brine. The organic layer was separated, dried over magnesium sulfate, filtered and solvents removed in vacuo. The residue was purified by medium pressure liquid chromatography on silica, eluting with ethyl acetate/hexane (2:1) to afford 56 mg of product in addition to 22 mg (0.05 mmol, 24%) recovered starting material. NMR analysis reveals the product to be a mixture of 85% mono methyl and 15% dimethyl derivatives.

NMR 300MHz, $CDCl_3$: 0.87 (t,3h, 1.20 (s,,9H), 1.21 (t,3h), 1.33 (m,2H), 1.62 (m,2H), 2.59 (t,2HO, 2.04 (d,3H), 4.17 (q,2H), 5.43 s,2H, 5.55 (br s, 1H), 7.02 (d,2H), 7.23 (d,2H), 7.24 (d,1H), 7.36 (t,1H), 7.45 (t,1H), 7.74 (d,1H).

FAB-MSS: 492 (M+H, 48%): monomethyl, 505 (M+, 22%): dimethyl

Step B: Preparation of 2-butyl-4-methylamino-5-carboethoxy-1-(2'-carboxybiphen-4-yl)methyl-imidazole To a solution of 56 mg (ca. 0.11 mmol) of the mixture of intermediates described in Step A above in 2 mL methylene chloride at room temperature was added two drops of anisole followed by 2 mL anhydrous trifluoroacetic acid. After three hours, all volatiles were removed in vacuo and the residue purified by reverse phase HPLC on C18 eluting with methanol/0.1% aqueous trifluoroacetic acid (linear gradient: 80% methanol to 85% methanol over 10 minutes). In this manner, 33 mg (0.080 mmol, 66%) of the title compound was obtained in addition to 9 mg (0.02 mmol, 17%) of the dimethyl derivative.

NMR (300MHz, $CD_3OD$): 0.95 (t,3H), 1.26 (t,3H), 1.41 (m,2H), 1.59 (m,2H), 2.93 (t,2H), 3.08 (s,3H), 4.30 (q,2H), 5.73 (s,2H), 7.20 (d,2H), 7.38 (d,3H), 7.48 (t,1H), 7.59 (t,1H), 7.85 (d,1H).

FAB-MS: 436 (+H, 100%).

EXAMPLE 14

2-Butyl-4-dimethylamino-5-carboethoxy-1-(2-carboxybiphen-4-yl)methylimidazole

The title compound (9 mg, 13%) was obtained by the procedures described in Example 13 (Step B).

NMR (300MHz, $CDCl_3$: 0.94 (t,3H), 1.26 (t,3H), 1.42 (m,2H), 1.61 (m,2H), 2.95 (t,2H), 3.14 (s,6H), 4.29 (q,2H), 5.77 (s,2H), 7.19 (d,2H), 7.38 (d,3H), 7.48 (t,1H), 7.60 (t,1H), 7.86 (d,1H).

FAB-MS: 450 (M+H, 100%).

EXAMPLE 15

4-Acetamido-2-butyl-1-(2'-(tetrazol-5-yl)biphen-4-yl)-methylimidazole-5-carboxylic acid

Step 1

4-Amino-2-butyl-1-[(2'-(N-triphenylmethyl-tetrazol-5-yl)biphen-4-yl)methyl]-5-(tert-butoxycarbonyl)imidazole The title compound was prepared by using the procedures outlined in Example 1 substituting t-butylglycinate hydrochloride for the corresponding methyl ester in Step C. $^1H$ NMR (300 MHz, $CDCl_3\delta$ 7.85 (d, 1H), 7.63-7.58 (m, 2H), 7.44 (d, 1H), 7.05 (d, 2H), 6.72 (d, 2H), 5.22 (s, 2H), 2.22 (t, 2H), 1.48-1.35 (m, 2H), 1.34 (s, 9H), 1.22-1.09 (m, 2H), 0.73 (t, 3H).

Step 2

4-Acetamido-2-butyl-1-[(2'-(N-triphenyl-methyltetrazol-5-yl)biphen-4-yl)methyl]-5-(tert-butoxycarbonyl)imidazole The title compound was prepared by using the procedures outlined in Example 5, Step A. 1H NMR (300 MHz, $CDCl_3\delta$ 7.86 (d. 1H). 7.52-7.40 (m, 2H), 7.36-7.22 (m, 10H), 7.10 (d, 2H), 6.96 (d, 2H), 5.38 (s, 2H), 2.52 (s(b), 3H), 2.32 (t'2H), 1.70-1.56 (m, 2H), 1.42 (s, 9H), 1.35-1.20 (m, 2H), 0.86 (t, 3H).

Step 3

4-Acetamido-2-butyl-1-(2'-(tetrazol-5-yl)-biphen-4-yl)methylimidazole-5-carboxylic acid A mixture of the Step 2 material (51 mg) and 85% formic acid (2 mL) was stirred at room temperature for 36 hours. Concentration (in vacuo at room temperature) and purification ($SiO_2$, 35:65:1 $CH_2Cl_2$/MeOH/$NH_4OH$) gave the title compound (10 mg) as a solid. FAB MS (M++1)=460, (M++Na)=482; 1H NMR (300 MHz, $CDCl_3\delta$ 7.63-7.35 (m, 4H), 7.06-6.86 (ABq, 4H), 5.73 (s, 2H), 2.74-2.60 (m, 2H), 2.02 (s(b), 3H), 1.48-1.22 (m, 4H), 0.83 (t, 3H).

EXAMPLE 16

2-Butyl-4-(N-methylacetamido)-1-(2'-(tetrazol-5-yl)-biphen-4-yl)methylimidazole-5-carboxylic acid

Step 1 5-(tert-Butoxycarbonyl)-2-butyl 4-(methylamino)-1-(2'-(N-triphenylmethyltetrazol-5-yl)biphen-4-yl)methylimidazole The title compound was prepared by using the procedures outline in Example 2, Step A starting from 4-amino-(5-tert-butoxycarbonyl)-2-butyl-1-(2'-(N-triphenylmethyltetrazol-5-yl)biphen-4-yl)methylimidazole.

Step 2

2-Butyl-4-(N-methylacetamido)-1-(2'-(tetrazol-5-yl)biphen-4-yl)methylimidazole-5-carboxylic acid The title compound was prepared by using the procedures outlined in Example 15, Steps 2 and 3.

FAB MS (M++1)=474, (M++Na)=496;

$^1H$ NMR (300 MHz, $CDCl_3\delta$ 7.58-7.48 (m, 4H), 7.12-6.88 (ABq, 4H), 5.69 (s, 2H), 3.18 (s, 3H), 2.62 (t, 2H), 1.90 (s, 3H), 1.65-1.50 (m, 2H), 1.40-1.28 (m, 2H), 0.89 (t, 3H).

EXAMPLE 17

2-Butyl-4-(methylamino)-1-(2'-(tetrazol-5-yl)biphen-4-yl)methylimidazole-5-carboxylic acid The title compound can be prepared from 2-butyl-4-(N-methylacetamido)-1-(2'-(tetrazol-5-yl)-biphen-4-yl)methylimidazole-5-carboxylic acid by reaction with 3 molar equivalents of diisobutyl-aluminum hydride in THF at room temperature followed by aqueous workup (extraction from 0.1% aqueous HOAc with EtOAc and isolation (SiO$_2$, 35:65:1 CH$_2$Cl$_2$/MeOH/ NH$_4$OH). Alternatively' the title compound could be prepared from 4-methylamino-5-benzyloxycarbonyl-2-butyl-1-(2'-(N-triphenylmethyltetrazol-5-yl-biphen-4-yl)methylimidazole (mentioned in Example 18, Step 2) by reaction as outlined in Example 18, Step 3.

EXAMPLE 18

2-Butyl-4-(dimethylamino)-1-(2'-(tetrazol 5-yl)biphen-4-yl)methylimidazole-5-carboxylic acid

Step 1
4-Amino-5-benzyloxycarbonyl-2-butyl-1-(2'-(N-triphenylmethyltetrazol-5-yl)biphen-4-yl)methylimidazole The title compound can be prepared by using the procedures outlined in Example 1 substituting benzylglycinate hydrochloride for the corresponding methyl ester in Step C.

Step 2
4-(Dimethylamino)-5-benzyloxycarbonyl-2-butyl-1-(2'-(N-triphenylmethyltetrazol-5-yl)biphen-4-yl)methylimidazole The title compound can be prepared by using the procedures outlined in Example 3 starting from 4-amino-5-benzyloxycarbonyl-2-butyl-1-(2'-(N-triphenylmethyltetrazol-5-yl)biphen-4-yl)methylimidazole. A side product in this reaction would be 4-methyl-amino-5-benzyloxycarbonyl-2-butyl-1-(2'(N-triphenyl-methyltetrazol-5-yl)biphen-4-yl)methylimidazole.

Step 3
4-(Dimethylamino)-2-butyl-1-(2'-(tetrazol-5-yl)biphen-4-yl)methylimidazole-5-carboxylic acid The title material can be prepared by treating a mixture of 4-(dimethylamino)-2 butyl 5-benzyloxycarbonyl-1-(2'-(N-triphenylmethyltetrazol-5-yl)biphen 4-yl)methylimidazole and 5 weight % of 10% Pd-C with H$_2$ (at 40 psi) in EtOH for 16 hours, followed by filtration (Celite) and purification (SiO$_2$'35:65:1 CH$_2$Cl$_2$/MeOH/NH$_4$OH).

EXAMPLE 19

2-Butyl-4-(pyrrilidin-1-yl)-1-(2'-(tetrazol-5-yl)-biphen-4-yl)methylimidazole-5-carboxylic acid

Step 1
5-Benzyloxycarbonyl-2-butyl-4-(pyrrolidin-1-yl)-1-(2'-(N-triphenylmethyltetrazol-5-yl)biphen-4-yl)methylimidazole The title compound could be prepared by using the procedure outlined in Example 4, Step A starting from 4-amino-5-benzyloxycarbonyl-2-butyl-1-(2'-(N-triphenylmethyltetrazol-5-yl)biphen-4-yl) methylimidazole.

Step 2 2
Butyl-4-(pyrrolidin-1-yl)-1-(2'-(tetrazol-5-yl)biphen-4-yl)methylimidazole-5-carboxylic acid The title compound could be prepared by using the procedure outlined in Example 18, Step 3.

EXAMPLE 20

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-butyl-4-methyl-1-(2'-(tetrazol-5-yl)biphen-4-yl)methyl-1,4,6,7-tetrahydroimidazo[4,5-e]-[1,4]diazepine-5,8-dione | 50 |
| Lactose | 149 |
| Magnesium stearate | 1 |
| Capsule (size No. 1) | 200 |

The 2-butyl-4-methyl-1-(2'-(tetrazol-5-yl) biphenyl]-4-yl)methyl-1,4,6,7-tetrahydroimidazo[4,5-e]-[1,4]-diazepine-5,8-dione can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-butyl-4-methyl-1 (2'(tetrazol-5-yl)biphen-4-yl) methyl-1,4,6,7-tetrahydroimidazo[4'5-e]-[1.4]diazepine 5,8-dione (25 mg), pregelatinized starch USP (82 mg), microcrystaline cellulose 82 mg and magnesium stearate (1 mg).

C: Combination Tablet

A typical combination tablet would contain, for example, a diuretic such as hydrochlorothiazide and consist of 2-butyl-4-methyl-1-(2'-(tetrazol-5-yl) biphen-4-yl)methyl-1,4'6,7-tetrahydroimidazo[4,5-e]-[1,4]-diazepine-5,8-dione hydrochlorothiazide (50 mg), pregelatinized starch USP (82 mg), microcrystalline cellulose (82 mg) and magnesium stearate (1 mg).

D: Suppository

Typical suppository formulations for rectal administration can contain 2-butyl-4-methyl-1-(2'-(tetrazol-5-yl)biphen-4-yl)methyl-1,4,6,7-tetrahydro-imidazo[4,5-e]-[1,4]-diazepine-5,8-dione butylated hydroxyanisol (0.08–1.0 mg), disodium calcium edetate (0.25–0.5 mg), and polyethylene glycol (775–1600 mg). Other suppository formulations can be made by substituting, for example butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 2-butyl-4-methyl-1-(2'-(tetrazol-5-yl) biphen-4-yl)methyl-1,4,6,7-tetrahydroimidazo[4,5-e]-[1,4]diazepine-5,8-dione sodium phosphate dibasic anhydrous (11.4 mg) benzylalcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of formula (II):

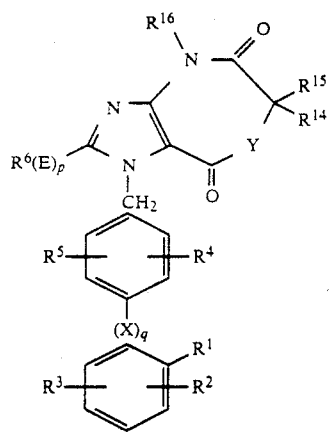

wherein:
$R^1$ is
(a) carboxy,
(b) $C_1$-$C_4$-alkoxycarbonyl,
(c) —NHSO$_2$CF$_3$, or

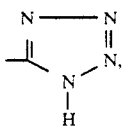

(e) —PO(OR$^9$)R$^9$,
(f) —PO(OR$^9$)$_2$,
(g) —SO$_2$NH-heteroaryl,
(h) —CH$_2$CO$_2$NH-heteroaryl,
(i) —SO$_2$NH—CO—R$^{25}$,
(j) —CH$_2$SO$_2$NH—CO—R$^{25}$,
(k) —CONH—SO$_2$R$^{25}$,
(l) —CH$_2$CONH—SO$_2$R$^{25}$,
(m) —NHSO$_2$NCHO—R$^{25}$,
(n) —NHCONHSO$_2$R$^{25}$,
(o) —SO$_2$NHCONHR$^{25}$;

$R^2$ and $R^3$ are independently
(a) hydrogen,
(b) $C_1$-$C_4$-alkyl, or
(c) halo;

$R^4$ and $R^5$ are independently
(a) hydrogen,
(b) $C_1$-$C_6$-alkyl,
(c) $C_1$-$C_6$-alkoxy, or
(d) halo;

$R^6$ is
(a) $C_1$-$C_6$-alkyl,
(b) $C_1$-$C_6$-alkenyl,
(c) $C_1$-$C_4$-alkoxy-$C_1$-$C_6$-alkyl,
(d) $C_1$-$C_4$-alkylthio-$C_1$-$C_6$-alkyl,
(e) $C_1$-$C_4$-alkoxy-$C_1$-$C_6$-alkenyl, or
(f) $C_1$-$C_4$-alkylthio-$C_1$-$C_6$-alkenyl;

E is —S—;
p is 0 or 1;
X is

(b) —S—or
(c) —OCH$_2$—;
q is 0 or 1;
$R^{14}$ is H;
$R^{15}$ is
(a) H,
(b) $C_1$-$C_6$-alkyl,
(c) substituted $C_1$-$C_6$-alkyl wherein the substituent is selected from the group consisting of
(i) hydroxy,
(ii) amino,
(iii) guanidino,
(iv) $C_1$-$C_4$-alkylthio,
(v) carboxy,
(vi) carboxamido,
(vii) $C_1$-$C_4$-alkoxycarbonyl, or

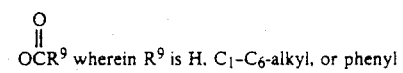

(d) benzyl,
(e) 4-hydroxybenzyl,
(f) 3-indolylmethyl,
(g) 4-imidazolylmethyl, or
(h) phenyl; and $R^{16}$ is H or $C_1$-$C_4$-alkyl
Y is
(a) —O—,

2. A compound of claim 1 wherein: $R^2$, $R^3$, $R^4$ and $R^5$ are hydrogen; and p and q are zero.

3. A compound of claim 2 wherein:
$R^1$ is
(a) carboxy,
(b) $C_1$-$C_4$-alkoxycarbonyl,

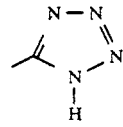

4. A compound of claim 3 wherein:
$R^6$ is $C_1$-$C_6$-alkyl,
$R^{15}$ and $R^{16}$ are each hydrogen;
Y is —NH—.

5. A compound of claim 4 selected from the group consisting of:
(1) 2-butyl-1-(2'-carboxybiphen-4-yl)-methyl-1,4,6,7-tetrahydroimidazo[4,5-e]-[1,4]diazepine-5,8-dione; and, (2) 2-butyl-1-(2'-(tetrazol-5-yl)biphen-4-yl)methyl-1,4,6,7-tetrahydroimidazo[4,5-e]-[1,4]diazepine-4-methyl-5,8-dione.

6. A pharmaceutical composition useful in the treatment of hypertension which comprises a pharmaceutically acceptable carrier an a pharmaceutically effective amount of a compound of claim 1.

7. A method of treating hypertension which comprises administering to a patient in need of such treatment a pharmaceutically effective amount of a compound of claim 1.

8. An ophthalmalogical formulation for the treatment of ocular hypertension comprising an ophthalamologically acceptable carrier and an effective ocular antihypertensive amount of a compound of claim 1.

9. A method of treating ocular hypertension comprising administering to a patient in need of such treatment an effective ocular antihypertensive amount of a compound of claim 1.

* * * * *